US007943654B2

(12) United States Patent
Fancelli et al.

(10) Patent No.: US 7,943,654 B2
(45) Date of Patent: May 17, 2011

(54) 1H-THIENO[2,3-C]PYRAZOLE COMPOUNDS USEFUL AS KINASE INHIBITORS

(75) Inventors: Daniele Fancelli, Milan (IT); Jurgen Moll, Appiano Gentile (IT); Maurizio Pulici, Caponago (IT); Francesca Quartieri, Arona (IT); Tizizno Bandiera, Gambolò (IT)

(73) Assignee: Nerviano Medical Sciences S.R.L., Nerviano (IT)

( * ) Notice: Subject to any disclaimer, the term of this patent is extended or adjusted under 35 U.S.C. 154(b) by 204 days.

(21) Appl. No.: 11/988,528

(22) PCT Filed: Jul. 10, 2006

(86) PCT No.: PCT/EP2006/064055
§ 371 (c)(1),
(2), (4) Date: Jan. 9, 2008

(87) PCT Pub. No.: WO2007/009898
PCT Pub. Date: Jan. 25, 2007

(65) Prior Publication Data
US 2009/0149457 A1    Jun. 11, 2009

(30) Foreign Application Priority Data
Jul. 19, 2005 (EP) .................................... 05106602

(51) Int. Cl.
A01N 43/56 (2006.01)
A01N 43/06 (2006.01)
A61K 31/415 (2006.01)
A61K 31/38 (2006.01)
C07D 487/02 (2006.01)
C07D 231/54 (2006.01)
C07D 333/00 (2006.01)

(52) U.S. Cl. ..................... 514/407; 514/448; 548/360.5; 549/57

(58) Field of Classification Search .................. 514/407, 514/448; 548/360.5; 549/57
See application file for complete search history.

(56) References Cited

U.S. PATENT DOCUMENTS
2004/0110785 A1 * 6/2004 Wang et al. .................. 514/300
2005/0026984 A1    2/2005 Bigot et al.

FOREIGN PATENT DOCUMENTS
WO  WO 2004/007504 A1    1/2004
WO  WO 2004/013146 A1    2/2004
WO  WO 2004/013146      * 12/2004
WO  WO 2005/074922 A1    8/2005
WO  WO 2006/056697 A1    6/2006

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (1381, 1383-1385, and 1388 provided).*
Pollard JR and Mortimore M, "Discovery and development of aurora kinase inhibitors as anticancer agents," Journal of Medicinal Chemistry, May 2009, 52(9), 2629-2651.*
van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*

* cited by examiner

*Primary Examiner* — San-ming Hui
*Assistant Examiner* — Paul Zarek
(74) *Attorney, Agent, or Firm* — Scully, Scott, Murphy & Presser, P.C.

(57) ABSTRACT

There are provided thieno[2,3-c]pyrazole derivatives of formula (I), wherein A is an aryl or heteroaryl ring, on which the substituent-NHZR$_5$ is at the ortho position to the CONH linker; R$_1$ and R$_2$ are the same or different and, independently from each other, represent a hydrogen atom or an organic group; R$_4$ is a hydrogen or halogen atom or an organic group; Z is direct bond, >C=O, or —C(=O)NH—; R$_5$ is hydrogen or an organic group; or isomers, tautomers, carriers, metabolites, prodrugs, and pharmaceutically acceptable salts thereof. A process for their preparation and pharmaceutical compositions comprising them are also disclosed; the compounds of the invention may be useful, in theraphy, in the treatment of diseases associated with a disregulated protein kinase activity, like cancer.

18 Claims, No Drawings

1H-THIENO[2,3-C]PYRAZOLE COMPOUNDS USEFUL AS KINASE INHIBITORS

CROSS REFERENCE TO RELATED APPLICATIONS

The present application is a '371 application of PCT Application having Serial No. PCT/EP2006/064055, filed on Jul. 10, 2006, which claims the benefit of European Patent Application EP 05106602.5, filed Jul. 19, 2005.

BACKGROUND OF THE INVENTION

1. Field of the Invention

The present invention relates to thieno-pyrazole derivatives, to a process for their preparation, to pharmaceutical compositions comprising them, and to their use as therapeutic agents, particularly in the treatment of cancer and cell proliferation disorders.

2. Discussion of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Among the several protein kinases known in the art as being implicated in the growth of cancer cells are Aurora kinases, in particular Aurora-2.

Aurora-2 was found to be over-expressed in a number of different tumor types. Its gene locus maps at 20q13, a chromosomal region frequently amplified in many cancers, including breast [Cancer Res. 1999, 59(9), 2041-4] and colon.

20q13 amplification correlates with poor prognosis in patients with node-negative breast cancer and increased Aurora-2 expression is indicative of poor prognosis and decreased survival time in bladder cancer patients [J. Natl. Cancer Inst., 2002, 94(17), 1320-9]. For a general reference to Aurora-2 role in the abnormal centrosome function in cancer see also Molecular Cancer Therapeutics, 2003, 2, 589-595.

The insulin-like growth factor 1 receptor (IGF-1R, IGF1R) is a member of the insulin receptor subfamily of RTKs.

There exist several lines of evidence suggesting that IGF-1R signaling can contribute to tumorigenesis, and that interfering with IGF-1R function represents a valid therapeutic option in cancer. Forced expression of the receptor leads to ligand-dependent transformed growth of murine and of rat fibroblasts (e.g. Kaleko M., Rutter W. J. and Miller A. D. Mol Cell Biol vol. 10, pages 464-73, 1990; Rubini M., Hongo A., D'Ambrosio C. and Baserga R. Exp Cell Res vol. 230, pages 284-92, 1997), and such transformed cells are able to form tumors in vivo, with both in vitro transformation and tumor formation in vivo being dependent upon an active kinase domain (reviewed in Blakesley V. A., Stannard B. S., Kalebic T., Helman L. J., and LeRoith D. J Endocrinol vol. 152, pages 339-44, 1997).

SUMMARY OF THE INVENTION

It is an object of the invention to provide compounds, which are useful in therapy as agents against a host of diseases caused by and/or associated to a disregulated protein kinase activity and, more particularly, Aurora kinases activity or IGF-1R activity.

It is another object to provide compounds, which are endowed with protein kinase inhibiting activity and, more particularly, Aurora kinases or IGF-1R inhibiting activity. The present invention in particular relates to novel thieno-pyrazole compounds, and derivatives thereof, endowed with very high Aurora-2 kinase inhibiting activity. More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs and Aurora kinases in the regulation of cellular proliferation, these thieno-pyrazole derivatives are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

Accordingly, in a first embodiment, the present invention provides a compound of formula (I)

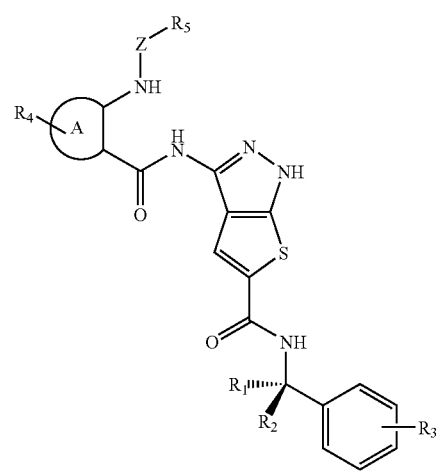

wherein

A is an aryl or heteroaryl ring, on which the substituent —NHZR$_5$ is at the ortho position to the CONH linker;

R$_1$ and R$_2$ are the same or different and, independently from each other, represent a hydrogen atom, a straight or branched C$_1$-C$_3$ alkyl or a group —CONH$_2$, —CH$_2$OR' or —CH$_2$NR'R'' or, taken together with the carbon atom to which they are bonded, R$_1$ and R$_2$ may form a C$_3$-C$_6$ cycloalkyl group; R' and R'' are the same or different and, independently from each other, represent a hydrogen atom or a straight or branched C$_1$-C$_3$ alkyl group or, taken together with the nitrogen atom to which they are bonded, R' and R'' may form a heterocyclic ring of formula

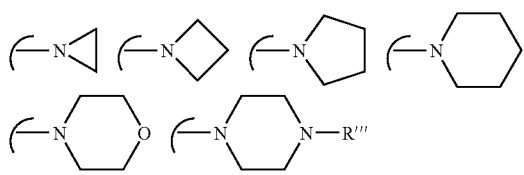

wherein R''' is a hydrogen atom or a straight or branched C$_1$-C$_3$ alkyl group;

R$_3$ is a hydrogen or halogen atom or a group selected from hydroxy, cyano, straight or branched C$_1$-C$_3$ alkyl, C$_1$-C$_6$ alkylamino, C$_1$-C$_6$ di-alkylamino and C$_1$-C$_3$ alkoxy;

R$_4$ is a hydrogen or halogen atom or a group selected from hydroxy, straight or branched C$_1$-C$_3$ alkyl, C$_1$-C$_3$ alkoxy, C$_1$-C$_6$ alkylamino, C$_1$-C$_6$ dialkylamino, azetidin-1-yl, pyrrolidin-1-yl, piperidin-1-yl, (1-methyl-piperazin-4-yl), (morpholino-4-yl), (azetidin-1-yl)methyl, (pyrrolidin-1-yl)methyl, (piperidin-1-yl)methyl, (1-methyl-piperazin-4-yl) methyl, (morpholino-4-yl)methyl, (1-methyl-piperidin-4-yloxy)methyl, (C$_1$-C$_6$ alkylamino)methyl and (C$_1$-C$_6$ di-alkylamino)methyl;

Z is direct bond, >C=O, or —C(=O)NH—;

R$_5$ is hydrogen or an optionally substituted group selected from C$_1$-C$_6$ alkyl, C$_3$-C$_6$ cycloalkyl, C$_2$-C$_6$ alkenyl, aryl, heteroaryl and saturated heteroaryl;

or isomers, tautomers, carriers, metabolites, prodrugs, and pharmaceutically acceptable salts thereof.

Accordingly, in a second embodiment, the present invention provides a method for treating cell proliferative disorders caused by and/or associated with an altered protein kinase activity, which comprises administering to a mammal in need thereof an effective amount of a compound of formula (I) as above defined.

The above method enables treatment of cell proliferative disorders caused by and/or associated with altered protein kinases, e.g. Aurora kinases or IGF-1R activity.

In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

The present invention also includes methods of synthesizing the thieno-pyrazole compounds of formula (I) and the pharmaceutically acceptable salts, as well as the pharmaceutical compositions comprising them.

A more complete appreciation of the invention and many of the attendant advantages thereof will be readily obtained as the same becomes better understood by reference to the following detailed description.

DETAILED DESCRIPTION OF THE INVENTION

Several heterocyclic compounds are known in the art as protein kinase inhibitors.

As an example, 2-carboxamido-pyrazole and 2-ureidopyrazole derivatives have been disclosed as protein kinase inhibitors in the international patent applications WO 01/12189, WO 01/12188, WO 02/48114 and WO 02/70515, all in the name of the Pharmacia Italia SpA.

Fused bicyclic compounds comprising pyrazole moieties and possessing kinase inhibitory activity have been also disclosed in WO 00/69846, WO 02/12242, WO 03/028720, WO 03/097610, WO 04/007504, WO 04/013146 and US2005/0026984

In addition, 5-phenylsulfonyl-thieno[2,3-c]pyrazole derivatives are also known in the art as synthetic intermediates for the preparation of more complex heterocyclic structures, as reported in Monatshefte fur Chemie 128, 687-696 (1997).

The compounds of formula (I) of the invention have asymmetric carbon atoms and may therefore exist as individual optical isomers, as racemic mixtures or as any other mixture comprising a majority of one of the two optical isomers, which are all to be intended as within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

Prodrugs or carriers are any covalently bonded compounds, which release the active parent drug, according to formula (I), in vivo. In cases when compounds may exist in tautomeric forms, each form is contemplated as being included within this invention whether existing in equilibrium or predominantly in one form.

As such, unless otherwise provided, when only one of the following tautomeric forms of formula (Ia) or (Ib) is indicated, the remaining one has still to be intended as comprised within the scope of the invention:

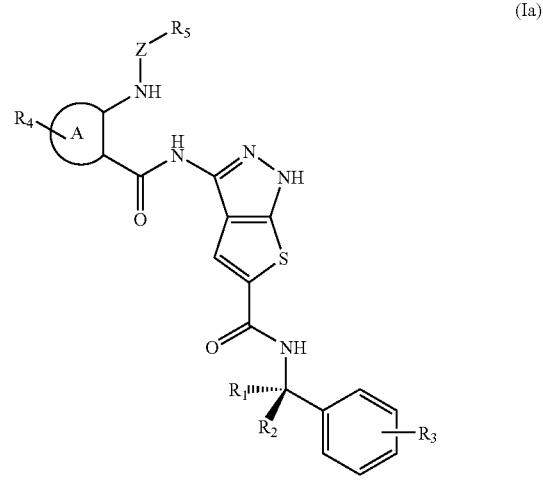

(Ia)

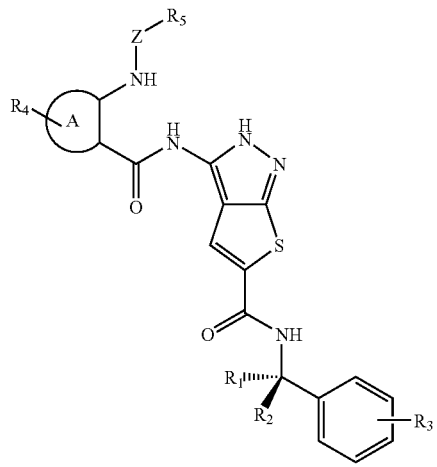

In the present description, unless otherwise specified, with the term aryl group we intend any aromatic carbocyclic ring system of 1 or 2 ring moieties, either fused or linked to each other through a single bond, for instance including phenyl, α- or β-naphthyl or biphenyl groups.

With the term heteroaryl we intend any aromatic heterocyclic ring which may comprise an optionally benzocondensed 5 or 6 membered heterocycle with from 1 to 3 heteroatoms selected among N, O or S.

Non limiting examples of heteroaryl groups according to the invention may thus include, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

With the term saturated heteroaryl we intend any saturated or partially unsaturated heteroaryl as above defined. Non limiting examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, azabicyclononane and the like.

With the term straight or branched $C_1$-$C_3$ alkyl or $C_1$-$C_3$ alkoxy we intend any of the groups such as methyl, ethyl, n-propyl, isopropyl, methoxy, ethoxy, n-propoxy and isopropoxy.

With the term halogen atom we intend a fluorine, chlorine, bromine or iodine atom.

With the term $C_3$-$C_6$ cycloalkyl we intend any group such as cyclopropyl, cyclobutyl, cyclopentyl or cyclohexyl. Clearly, as these same cycloalkyl groups may be formed when $R_1$ and $R_2$ are taken together with the carbon atom to which they are attached, cyclic spiro compounds may be thus obtained. Just as an example, when $R_1$ and $R_2$ together form a cyclopentyl group, derivatives having the following general formula are herewith considered:

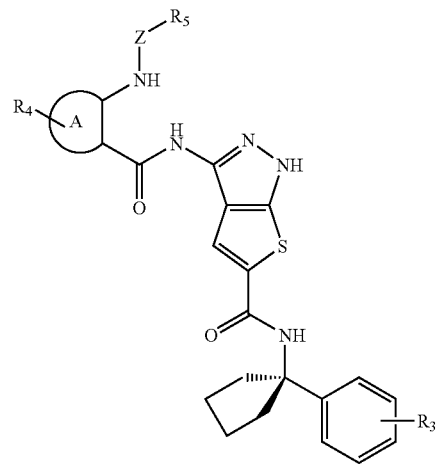

When considering derivatives of formula (I) wherein $R_1$ or $R_2$ represents a group —$CH_2NR'R''$ and R' and R'' are linked together with the nitrogen atom to which they are attached, heterocyclic moieties may be thus formed as per the general formula. Just as an example, by considering $R_1$ as hydrogen and $R_2$ as a group —$CH_2NR'R''$ with R' and R'' linked together so as to form a pyrrolidinyl-1-yl group, compounds having the following general formula are herewith considered:

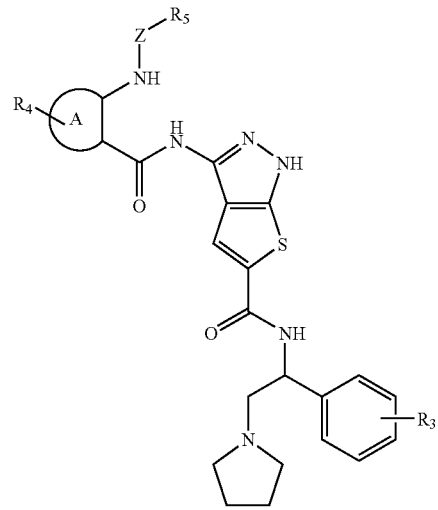

The inventors have surprisingly found a new class of compounds of formula (I) as defined above endowed with high protein kinases inhibition activity. The characterizing feature of the compounds of formula (I) of the present invention is an aryl or heteroaryl ring A on which the substituent —$NHZR_5$ is at the ortho position to the CONH linker. According to the meanings provided to the substituents, any of the above aryl or heteroaryl groups may be optionally further substituted in any of their free positions by one or more groups, for instance 1 to 6 groups, selected from: halogen, nitro, oxo groups (═O), carboxy, cyano, alkyl, polyfluorinated alkyl, alkenyl, alkynyl, cycloalkyl, cycloalkenyl; aryl, heterocyclyl, alkylheterocyclyl, heterocyclyl-alkyl, amino groups and derivatives thereof such as, for instance, alkylamino, dialkylamino, arylamino, diarylamino, ureido, alkylureido or arylureido;

carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, heterocylyloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

With the term alkyl or alkoxy group we intend, unless otherwise provided, any straight or branched $C_1$-$C_6$ alkyl or alkoxy group, hence comprehensive of the aforementioned $C_1$-$C_3$ alkyl or alkoxy groups and also comprising n-butyl, iso-butyl, sec-butyl, tert-butyl, n-pentyl, n-hexyl, n-butoxy, iso-butoxy, sec-butoxy, tert-butoxy, n-pentyloxy, n-hexyloxy, and the like.

With the term $C_2$-$C_6$ alkenyl or alkynyl group we intend, unless otherwise provided, any unsaturated straight or branched $C_2$-$C_6$ alkenyl or alkynyl group such as, for instance, vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term polyfluorinated alkyl or alkoxy we intend any straight or branched $C_1$-$C_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

With the term heterocycle, heterocyclyl or heterocyclic group we also intend an optionally benzocondensed 4 to 7 membered heterocycle, hence encompassing aromatic heterocyclic groups also known as heteroaryl groups, either saturated or partially unsaturated, with from 1 to 3 heteroatoms selected among N, O and S.

Examples of these 4 or 7 membered heterocyclic groups are, for instance, 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine, azetidine, and the like.

With the term cycloalkenyl we intend any of the aforementioned $C_3$-$C_6$ cycloalkyl groups further comprising a double bond such as, for instance, 2-cyclopenten-1-yl, 3-cyclopenten-1-yl, 1-cyclohexen-1-yl, 2-cyclohexen-1-yl, 3-cyclohexen-1-yl, and the like.

From all of the above, it is clear to the skilled man that any group which name has been identified as a composite name such as, for instance, alkylamino, dialkylamino, cycloalkylalkyl, arylalkyl, heterocyclylalkyl, alkylthio, aryloxy, arylalkyloxy, alkylcarbonyloxy and the like, has to be intended as conventionally construed from the parts to which they derive. So far, as an example, the term alkoxy-heterocyclyl-alkyl stands for a straight or branched alkyl group substituted by a heterocycle further substituted by alkoxy, wherein alkyl, heterocycle and alkoxy are as above defined. Likewise, the term alkyl-heterocyclyloxy stands for a heterocyclyloxy group further substituted by alkyl.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic or organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, arylaliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A preferred class of compounds of the invention is represented by the derivatives of formula (I) wherein A is a group selected from thienyl, furyl, pyrrolyl and phenyl.

More preferably, within the above class of compounds of formula (I), A is a phenyl ring substituted at position 2 by NH—Z—$R_5$ and substituted at position 4 by a group $R_4$ choosen from hydrogen, halogen, methoxy, azetidin-1-yl, pyrrolidin-1-yl, piperidin-1-yl, (1-methyl-piperazin-4-yl), (morpholino-4-yl), (azetidin-1-yl)methyl, (pyrrolidin-1-yl)methyl, (piperidin-1-yl)methyl, (1-methyl-piperazin-4-yl)methyl, (morpholino-4-yl)methyl, (1-methyl-piperidin-4-yloxy)methyl, ($C_1$-$C_6$ alkylamino)methyl and ($C_1$-$C_6$ di-alkylamino)methyl.

Even more preferably, within the above class of compounds of formula (I), Z is >C=O. Another preferred class of compounds of the invention is represented by the derivatives of formula (I) wherein $R_1$ and $R_2$ are both a methyl group or wherein $R_1$ and $R_2$, together with the carbon atom to which they are attached, form a $C_3$-$C_6$ cycloalkyl. Another preferred class of compounds of the invention is represented by the derivatives of formula (I) wherein A, Z, $R_1$, $R_2$ and $R_4$ are as set forth above and $R_3$ represents a hydrogen or halogen atom.

For a reference to any specific compound of formula (I) of the invention, optionally in the form of a pharmaceutically acceptable salt, see the following experimental section.

As formerly indicated, a further object of the present invention is represented by a process for preparing the compounds of formula (I) and the pharmaceutically acceptable salts thereof, which process comprises:

a) reacting a compound of formula (II),

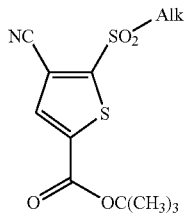

wherein Alk represents a straight or branched $C_1$-$C_6$ alkyl group, with hydrazine or a hydrazine salt and treating the resultant tert-butyl 4-cyano-5-hydrazinothiophene-2-carboxylate intermediate under acidic condition;
b) reacting the resultant cyclized compound of formula (III)

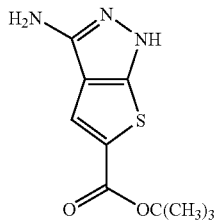

with any suitable pyrazole nitrogen atom protecting agent,
c) acylating the resultant compound of formula (IV)

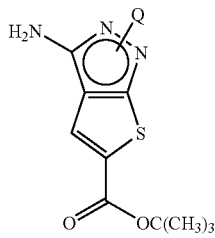

wherein Q represents the said protecting group with a compound of formula (V)

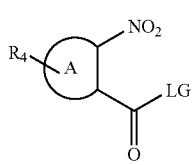

wherein A and $R_4$ are as defined above and LG represents a suitable leaving group, so as to obtain a compound of formula (VI), d) reducing the nitro group of the resultant compound of formula (VI)

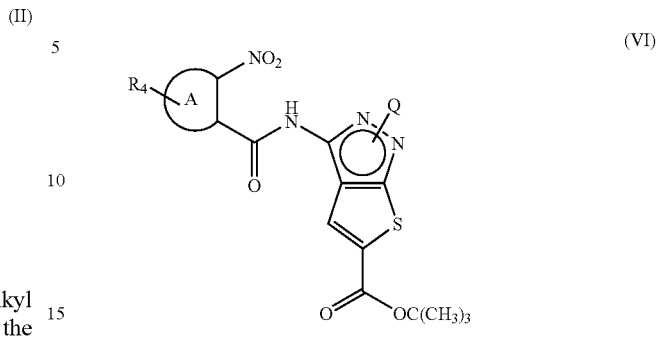

wherein A, $R_4$ and Q are as defined above, and
either
e) acylating the resultant compound of formula (VII)

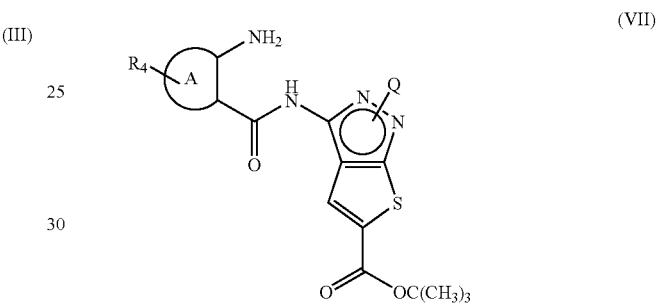

wherein A, $R_4$ and Q are as defined above, with a compound of formula $R_5$—Z-LG (VIII) or $R_5$—NCO (IX), when Z is >C=O or —C(=O)NH—, and $R_5$ and LG are as above defined; so as to obtain a compound of formula (X)

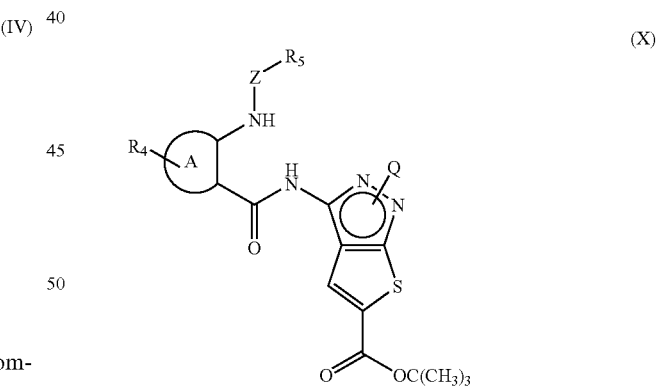

wherein A, $R_4$, $R_5$ and Q are as defined above, and Z is >C=O or —C(=O)NH—;
or
e') treating a compound of formula (VII) as defined above with a carbonyl compound of formula W—CO—Y (XI) wherein W and Y are hydrogen atoms or an optionally substituted group selected from $C_1$-$C_5$ alkyl, $C_1$-$C_5$ cycloalkyl, aryl, heteroaryl or saturated heteroaryl, in the presence of an opportune reducing agent, so as to obtain a compound of formula (X) as above defined wherein Z is a direct bond and
f) selectively hydrolyzing the tert-butyl ester group of the resultant compound of formula (X) as defined above;

g) reacting the resultant compound of formula (XII)

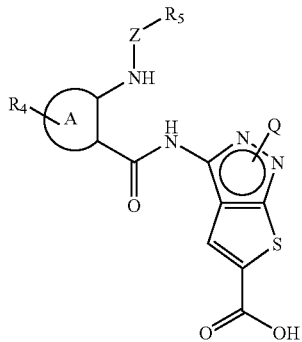
(XII)

wherein A, $R_4$, $R_5$ and Q are as defined above, and Z is as defined in formula (I) above, with a compound of formula (XIII)

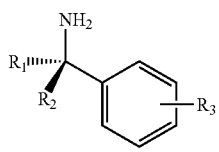
(XIII)

wherein $R_1$, $R_2$ and $R_3$ are as defined above, in the presence of any suitable condensing agent, and i) deprotecting the resultant compound of formula (XIV) by removing the Q pyrazole nitrogen atom protecting group:

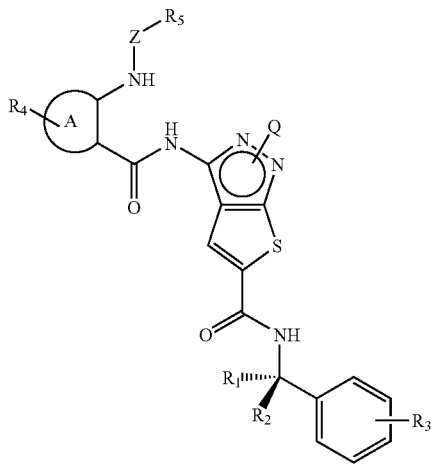
(XIV)

wherein A, $R_1$, $R_2$, $R_3$, $R_4$, $R_5$ and Q are as defined above, and Z is as defined in formula (I) above so as to obtain the compound of formula (I) and, whenever desired, converting the resultant compound of formula (I) as defined above into a different compound of formula (I) by well known reactions and if wanted, converting the compound of formula (I) as defined above into a pharmaceutically acceptable salt or converting the salt thereof into the free compound of formula (I) as defined above.

Alternatively, the compounds of the formula (I) of present invention may also be obtained by means of j) selectively hydrolyzing the tert-butyl ester group of the compound of formula (VI) as defined above;

k) reacting the resultant compound of formula (XV)

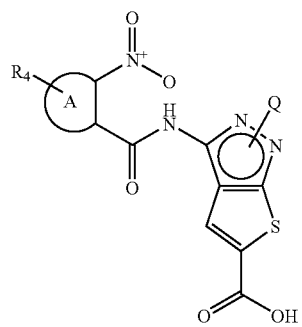
(XV)

wherein A, $R_4$ and Q are as defined above, with a compound of formula (XIII) as defined above, in the presence of any suitable condensing agent, and l) reducing the nitro group of the resultant compound of formula (XVI)

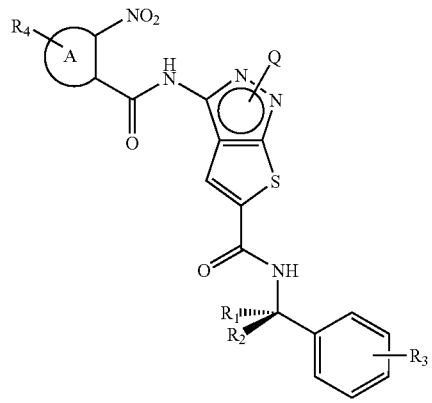
(XVI)

wherein A, $R_1$, $R_2$, $R_3$, $R_4$ and Q are as defined above, and either m) acylating the resultant compound of formula (XVII)

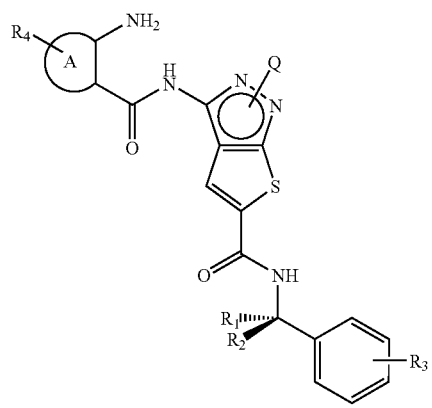
(XVII)

wherein A, $R_1$, $R_2$, $R_3$, $R_4$ and Q are as defined above, with a compound of formula $R_5$—Z-LG (VIII) or $R_5$—NCO (IX), when Z is >C=O or —C(=O)NH—, and R$_5$ and LG are as above defined; so as to obtain a compound of formula (XIV) as defined above wherein Z is >C=O or —C(=O)NH—; or m') treating a compound of formula (XVII) as defined above with a carbonyl compound of formula (XI) as defined above, in the presence of an opportune reducing agent, so as to obtain a compound of formula (XIV) as above defined wherein Z is a direct bond and finally deprotecting the resultant compound of formula (XIV) as described above under step i).

It is to be noted that a compound of formula (IV), (VII), (X), (XII), (XIV), (XV), (XVI) and (XVII) as above defined can be in any one of its tautomeric forms a or b:

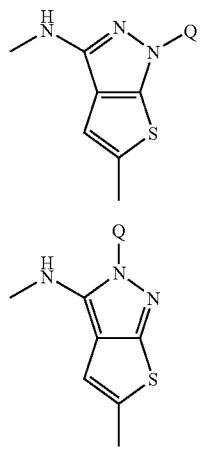

a b

The above process is an analogy process, which can be carried out according to methods known in the art.

From the above, it is clear to the person skilled in the art that if a compound of formula (I), prepared according to the above process, is obtained as an admixture of isomers, their separation into the single isomers of formula (I), carried out according to conventional techniques, is still within the scope of the present invention.

According to step (a) of the process, the reaction between a compound of formula (II) and hydrazine or a hydrazine salt, for instance hydrazine dihydrochloride or hydrazine sulphate or acetate, can be carried out in the presence of catalytic amounts of an acid such as hydrochloric, acetic or sulphuric acid, or in the presence of catalytic amounts of a Lewis acid such as boron trifluoride dimethyl etherate. Alternatively, this same reaction may be also accomplished in the presence of catalytic amounts of a strong base such as sodium methoxide.

The reaction is carried out in a suitable solvent such as, for instance, N,N'-dimethylformamide, tetrahydrofuran, 1,4-dioxane, acetonitrile, water, methanol or ethanol, at a temperature ranging from about room temperature to reflux and for a time varying from about 30 minutes to about 18 hours.

According to a preferred embodiment, within the compounds of formula (II), Alk represents a straight or branched lower alkyl group, for instance a C$_1$-C$_6$ alkyl group and even more preferably a C$_1$-C$_4$ alkyl group.

Preferably, step (a) is carried out by reacting a compound of formula (II) with hydrazine hydrate in methanol, ethanol or tetrahydrofuran at a temperature ranging from room temperature to refluxing temperature. The obtained tert-butyl 4-cyano-5-hydrazinothiophene-2-carboxylate intermediate can be either separated from the reaction medium and further processed as per the working examples or, alternatively, directly processed through cyclization so as to afford the compound of formula (III). Cyclization is carried out at a temperature ranging from about 15° C. to about 50° C. in methanol or ethanol, and in the presence of catalytic amounts of a mineral acid such as hydrochloric or sulphuric acid.

According to step (b) of the process, the thus obtained thieno-pyrazole derivative of formula (III) is then protected, according to well-known methods, at the pyrazole nitrogen atom. As an example, the above protection may occur with an alkyl chlorocarbonate, in a suitable solvent such as tetrahydrofuran, dichloromethane, chloroform, acetonitrile, toluene or mixtures thereof, at a temperature ranging from about −5° C. to about 35° C. and for a time varying from about 30 minutes to about 72 hours, in the presence of an opportune proton scavenger such as triethylamine or diisopropylethylamine.

According to step (c) of the process, the compound of formula (IV) is then reacted with any suitable acylating agent of formula (V) so as to yield the compound of formula (VI), by working according to methods well known in the art for the preparation of carboxamido derivatives. Typically, within the compound of formula (V), LG represents a halogen atom and, even more preferably, a bromine or chlorine atom.

The reaction is carried out in a suitable solvent such as, for instance, tetrahydrofuran, dimethylformamide, dichloromethane, chloroform, acetonitrile, toluene or mixtures thereof, at a temperature ranging from about −10° C. to reflux and for a time varying from about 30 minutes to about 96 hours, in the presence of an opportune proton scavenger such as triethylamine, N,N-diisopropylethylamine or pyridine.

From the above, it is clear to the skilled person that the above protection at the pyrazole nitrogen atom, in step (b), is of particular advantage as it prevents that acylation with the compound of formula (V), in step (c), occurs at the pyrazole nitrogen atom.

According to step (d) of the process, the aromatic nitro group of the compound of formula (VI) is reduced to amino. The reaction may be carried out in a variety of way and operative conditions, which are widely known in the art for reducing a nitro to an amino group. Preferably, this reaction is carried out in a suitable solvent such as, for instance, water, tetrahydrofuran, 1,4-dioxane, N,N-dimethylformamide, ethyl acetate, or a mixture thereof, in the presence of a suitable reducing agent, such as, for instance, hydrogen and a hydrogenation catalyst, or by treatment with cyclohexene or cyclohexadiene and a hydrogenation catalyst, or by treatment with tin (II) chloride, at a temperature ranging from 0° C. to reflux and for a time varying from about 1 hour to about 96 hours. The hydrogenation catalyst is usually a metal, most often palladium, which can be used as such or supported on carbon.

According to step (e) of the process, the compound of formula (VII) is then reacted with any suitable acylating agent of formula (VIII) or (IX) so as to yield the compound of formula (X), by working according to methods well known in the art for the preparation of carboxamido and ureido derivatives. Typically, within the compound of formula (VIII), LG represents a halogen atom, preferably a chlorine atom, or a 2,4-dinitro-phenoxy group.

The reaction is carried out in a suitable solvent such as, for instance, tetrahydrofuran, dimethylformamide, dichloromethane, chloroform, acetonitrile, toluene or mixtures thereof, at a temperature ranging from about −10° C. to reflux and for a time varying from about 30 minutes to about 96 hours. If needed, the reaction is carried out in the presence of an opportune proton scavenger such as triethylamine, N,N-diisopropylethylamine or pyridine.

According to step e') of the process, the reaction between a compound of Formula (VII) and an aldehyde or a ketone can be carried out in a variety of ways, according to conventional methods for carrying out reductive alkylation, to give a compound of formula (X) wherein Z is a direct bond. Preferably, this reaction is carried out in a suitable solvent such as, for instance, methanol, N,N-dimethylformamide, dichloromethane, tetrahydrofuran, or a mixture thereof, in the presence of a suitable reducing agents such as, for instance, sodium borohydride, tetra-alkylammonium borohydride, sodium cyano borohydride, sodium triacetoxyborohydride, tetramethylammonium triacetoxy borohydride, hydrogen and a hydrogenation catalyst, and in the presence of an acid catalyst, such as, for instance, acetic acid, trifluoroacetic acid, at a temperature ranging from about 0° C. to reflux and for a time varying from about 1 hour to about 96 hours.

According to step (f) of the process, the carboxyester function of the compound of formula (X) is selectively hydrolized so as to yield the corresponding carboxy group.

The reaction is carried out under acidic conditions, preferably in the presence of hydrochloric acid in dioxane, by operating at room temperature and for a suitable time, for instance up to 72 hours or by using up to 50% trifluoro acetic acid in dichloromethane.

According to step (g) of the process, the compound of formula (XII) is then reacted with a suitable amino derivative of formula (XIII) so as to lead to the corresponding compound of formula (XIV).

From the above it is clear to the skilled person that this reaction may be accomplished in a variety of ways and operative conditions, which are widely known in the art for the preparation of carboxamides.

As an example, the reaction between the compounds of formula (XII) and (XIII) can be carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole.

Alternatively, this same reaction can be also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

Finally, according to step (i) of the process, the compound of formula (XIV) is deprotected at the pyrazole nitrogen atom under basic conditions and by working according to conventional techniques, for instance by treatment with aqueous sodium or potassium hydroxide in the presence of a suitable co-solvent such as methanol, ethanol, dimethylformamide, 1,4-dioxane, or by treatment with a tertiary amine such as triethylamine or N,N-diisopropylethylamine and by using an alcohol like methanol or ethanol as the solvent.

Deprotection may occur at a temperature ranging from about 18° C. to refluxing temperature of the solvent, for a time varying from about 30 minutes to about 72 hours.

If desired, the salification of a compound of formula (I) or the conversion of a corresponding salt thereof into the free compound (I), according to step (f) of the process, can be easily carried out according to well-known methods in the art.

In the alternative preparation, the steps j), k), l), m) and m') can be carried out as described in detail above in the corresponding steps f), g), d), e) and e').

As it will be appreciated by the person skilled in the art, when preparing the compounds of formula (I) object of the invention, optional functional groups within both the starting materials or the intermediates thereof and which could give rise to unwanted side reactions, need to be properly protected according to conventional techniques. Likewise, the conversion of these latter into the free deprotected compounds may be carried out according to known procedures.

All of the compounds of formula (II), (V), (VIII), (IX) and (XI) are known or can be obtained according to known methods.

As an example, the starting material of formula (II) wherein Alk stands for methyl can be easily obtained as follows, by starting from commercially available ethyl 4-cyano-5-(methylthio)thiophene-2-carboylate:

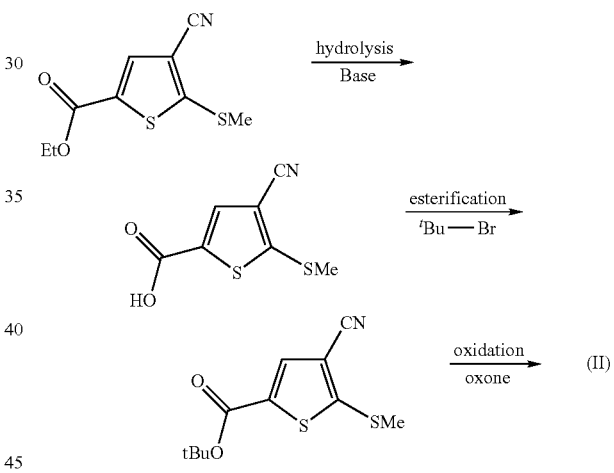

The hydrolysis of the ethoxycarbonyl group is carried out according to well-known methods, for instance in the presence of aqueous alkaline solutions such as aqueous sodium hydroxide.

Likewise, esterification is carried out according to well-known operative conditions, in the presence of an alkylating agent like tert-butyl bromide or di-tertbutyl-dicarbonate, in a suitable solvent such as dimethylformamide or tetrahydrofuran.

Finally, the conversion of the alkylthio group into alkylsulfonyl can be carried in the presence of any opportune oxidizing agent such as, for instance, hydrogen peroxide, 3-chloroperoxybenzoic acid or oxone, in a suitable solvent such as, for instance, dichloromethane, DMF, acetone, toluene, acetonitrile, methanol, ethanol, water, acetic acid, at a temperature ranging from about −10° C. to reflux and for a time varying from about 30 minutes to about 4 days.

For a general reference to the preparation of the compounds of formula (II) see, as an example, J. Bioorg. Med. Chem. Lett. 11 (2001), 915-918; EP-A-234622; as well as the following experimental section.

Pharmacology

The compounds of formula (I) are active as protein kinase inhibitors, more particularly as Aurora kinases inhibitors or IGF-R1 inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis.

The inhibiting activity and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay for IGF-1 R Kinase Activity

The buffers/components used in the assay were as follows. Kinase Buffer (buffer KB) was composed of 50 mM HEPES, 3 mM MnCl2, 1 mM DTT, 3 microM Na3VO4, pH 7.9. Enzyme Buffer (buffer EB) was composed of buffer KB containing 0.6 mg/ml BSA (bovine serum albumin). SPA scintillation beads (Product Code Number RPNQ0007, Amersham Biosciences, Piscataway, N.J. USA) were prepared as a 10 mg/ml suspension in PBS containing 32 mM EDTA, 500 microM unlabeled ATP, and 0.1% Triton X-100. This preparation is referred to below as "SPA bead suspension". On the day of assay, IGF-1R was pre-phosphorylated in order to linearize reaction kinetics. To achieve this, the desired quantity of enzyme was incubated for 30 min at 28° C. at a concentration of 1050 nM enzyme in buffer EB containing 100 microM unlabeled ATP. After preincubation, and immediately before assay, this pre-phosphorylated IGF-1R kinase preparation was diluted to an enzyme concentration of 60 nM by addition of 16.5 volumes of buffer KB. This diluted prephosphorylated enzyme is referred to below as "enzyme mix".

The substrate used in the assay was a carboxy-terminally biotinylated peptide of the following sequence: KKKSPGEYVNIEFGGGGGK-biotin (SEQ ID NO:1). The peptide was obtained in batches of >95% peptide purity from American Peptide Company, Inc. (Sunnyvale, Calif., USA). "ATP Mix", referred to below, consisted of buffer KB containing 6 nM 33Pg-ATP (gamma phosphate-labeled, Redivue™ Code Number AH9968, 1000-3000Ci/mmole, Amersham Biosciences Piscataway, N.J. USA), 18 microM unlabeled ATP, and 30 microM biotinylated substrate peptide. This solution contained these components at 3× their final reaction concentrations. Compounds to be tested were prepared in 100% DMSO at appropriate concentrations. These preparations were then diluted 33-fold using buffer KB so as to obtain compound at 3×preparation is referred to below as "compound working solution".

Kinase reaction: Reactions were performed in 96-well U-bottom microtiter plates (such as Product #650101, Greiner Bio-One, Kremsmuenster Austria) in a final reaction volume of 30 microL. To each test well were added 10 microL of "compound working solution" containing appropriate dilution of compound, followed by 10 microL "ATP Mix" and 10 microL "Enzyme Mix", thus starting the reaction. Well contents were immediately mixed by pipetting, and reactions were incubated for 60 minutes at room temperature. After incubation, reactions were stopped by adding 100 microL/well "SPA bead suspension". Wells were incubated a further 15 minutes at room temperature, then 110 microL were withdrawn from each well and transferred to separate wells of 96-well opaque scintillation counting plates (such as OptiPlate™-96, PerkinElmer LAS, Inc. Boston, Mass., USA), each containing 100 microL/well 5M CsCl. After 4 hours resting at room temperature to allow SPA bead floatation, these plates were read using a scintillation counter (Packard TopCount NXT, PerkinElmer LAS, Inc. Boston, Mass., USA) in order to quantitate the light emitted from each well (proportional to the amount of phosphate incorporated into the substrate peptide during kinase reaction).

Many of the steps described above, such as those involving compound dilution, addition of mixes to the reaction, and transfer of completed reaction to counting plates can be automated using robotized pipetting stations (such as Multimek and Biomek liquid handlers, Beckman Coulter Inc., Fullerton Calif. USA), and a dilution curve of a known kinase inhibitor such as staurosporine can be routinely included as a positive control for IGF-1R inhibition.

Results: data were analyzed using the "Assay Explorer" software package (Elsevier MDL, San Leandro, Calif. 94577). For single compound concentrations, inhibitory activity was typically expressed as expressed as % inhibition obtained in presence of compound, compared to total activity of enzyme obtained when inhibitor is omitted.

Compounds showing desired inhibition can be further analyzed in order to study the potency of the inhibitor through IC50 calculation. In this case, inhibition data obtained using serial dilutions of the inhibitor can be fitted by nonlinear regression using the following equation:

$$v = v_0 + \frac{(v_0 - v_b)}{1 + 10^{n(log IC_{50} - log[I])}}$$

where vb is the baseline velocity, v is the observed reaction velocity, vo is the velocity in the absence of inhibitors, and [I] is the inhibitor concentration.

Western Blot Analysis of Receptor Phosphorylation Following Stimulation with IGF-1 in MCF-7 Human Breast Cancer Cells MCF-7 cells (ATCC# HTB-22) were seeded in 12-well tissue culture plates at 2×10^5 cells/well in E-MEM medium (MEM+Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr1131/InsR Tyr1146 antibody (product #3021, Cell Signaling Technology, Beverly, Mass., USA) for the detection of phosphorylated IGF-1R, or 1/1000 dilution of rabbit IGF-Irβ(H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+ 0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts.

Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% CO2 in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed ×2 with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/500 Goat anti-rabbit Cy5™-conjugated secondary antibody (Amersham Biosciences, Little Chalfont, Buckinghamshire, UK). Wells were then washed ×2 with PBS, and 40 microL PBS are left in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St. Louis, Mo., USA.

Inhibition Assay of Aurora-2 Activity

Kinase reaction: 8 μM biotinylated peptide (4 repeats of LRRWSLG) (SEQ ID NO:2), 10 μM ATP (0.5 uCiP$^{33}$ γ-ATP), 7.5 ng Aurora 2, inhibitor in a final volume of 30 μl buffer (HEPES 50 mM pH 7.0, MgCl$_2$ 10 mM, 1 mM DTT, 0.2 mg/mL BSA, 3 μM orthovanadate) were added to each well of a 96 U bottom well plate. After 60 minutes at room temperature incubation, reaction was stopped and biotinylated peptide captured by adding 100 μl of bead suspension.

Stratification: 100 μl of CsCl 5 M were added to each well and let stand 4 hour before radioactivity was counted in the Top-Count instrument.

IC50 determination: inhibitors were tested at different concentrations ranging from 0.0015 to 10 μM. Experimental data were analyzed by the computer program GraphPad Prizm using the four parameter logistic equation:

$$y = \text{bottom} + (\text{top-bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM MgCl$_2$, 0.2 mg/mL BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq. 1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

The compounds of the invention were further tested, in vitro to assess the anti-proliferative effect onto cell cultures.

In Vitro Cell Proliferation Assay

The human colon cancer cell line HCT-116 was seeded at 5000 cells/cm$^2$ in 24 wells plate (Costar) using F12 medium (Gibco) supplemented with 10% FCS (EuroClone, Italy) 2 mM L-glutamine and 1% penicillin/streptomycin and maintained at 37° C., 5% CO$_2$ and 96% relative humidity. The following day, plates were treated in duplicates with 5 ul of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:

% of $CTR$=(Treated−Blank)/(Control−Blank).

$IC_{50}$ values were calculated by LSW/Data Analysis using Microsoft Excel sigmoidal curve fitting.

Given the above assays, the compounds of formula (I) of the invention resulted to possess a remarkable protein kinase inhibitory activity, e.g. Aurora-2 inhibitory activity. See, as an example, the following table I reporting the experimental data of some representative compounds of the invention being tested as Aurora-2 kinase inhibitors ($IC_{50}$ nM) and for their cell antiproliferative effect ($IC_{50}$ nM).

TABLE I

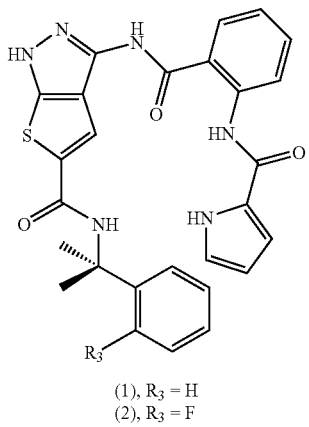

(1), $R_3$ = H
(2), $R_3$ = F

| Compound | Aurora-2 inhibition $IC_{50}$ (nM) | Cell Antiproliferation $IC_{50}$ (nM) |
| --- | --- | --- |
| (1) | 6 | 7 |
| (2) | 12 | 54 |

Compound (1) [Formula (I), $R_1$ = $R_2$ = methyl; $R_3$ = $R_4$ = H; Z = CO; $R_5$ = pyrrol-2-yl]: 3-{2-[(1H-pyrrole-2-carbonyl)-amino]-benzoylamino}-1H-thieno[2,3-c]pyrazole-5-carboxylic acid (1-methyl-1-phenyl-ethyl)-amide and
Compound (2) [Formula (I), $R_1$ = $R_2$ = methyl; $R_3$ = 2-F; $R_4$ = H; Z = CO; $R_5$ = pyrrol-2-yl]: 3-{2-[(1H-pyrrole-2-carbonyl)-amino]-benzoylamino}-1H-thieno[2,3-c]pyrazole-5-carboxylic acid [1-(2-fluoro-phenyl)-1-methyl-ethyl]-amide It is to be noted that the Aurora-2 inhibitory activity of the compounds (1) and (2) is surprisingly high. Moreover, the tested compounds resulted to possess also a very remarkable cell antiproliferative effect.

From all of the above, the novel compounds of formula (I) of the invention appear to be endowed with a biological profile, considered as a whole, which is unexpectedly superior to that of the prior art and, hence, are particularly advantageous, in therapy, against proliferative disorders associated with an altered kinase activity, in particular altered Aurora-2 kinase activity.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXPERIMENTAL SECTION

The following HPLC method was used in the analysis of the compounds, as specified in the synthetic examples set forth below. As used herein, the term "Rt" refers to the retention time (minutes) for the compound using the HPLC method specified below.

LC-MS Method

HPLC/MS was performed on a Waters X Terra RP 18 (4.6×50 mm, 3.5 μm) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was water/acetonitrile (5:95). Gradient from 10 to 90% B in 8 minutes, hold 90% B 2 min. UV detection at 220 nm and 254 nm. Flow rate 1 mL/min. Injection volume 10 μl. Full scan, mass range from 100 to 800 amu. Capillary voltage was 2.5 KV; Source temperature was 120° C.; Cone was 10 V. Retention Times (LC-MS Rt) are given in minutes at 220 nm or 254 nm. Mass are given as m/z ratio.

Example 1

4-Cyano-5-(methylthio)thiophene-2-carboxylic Acid

Aqueous sodium hydroxide (20% w/w solution, 9 mL) was added to a solution of ethyl 4-cyano-5-(methylthio)thiophene-2-carboxylate (10 g, 44 mmol) in 1,4-dioxane (100 mL) at 5° C.

After stirring for 4 hours at room temperature, water (500 mL) was added to the reaction mixture and the pH was adjusted to about 2.5 by adding 2N solution of aqueous hydrochloric acid. A white solid was separated by filtration, washed with water and dried under vacuum to give 8.5 g of the title compound.

LC-MS: Rt 2.4; $[M+H]^+$ 200.

Example 2

Tert-butyl 4-cyano-5-(methylthio)thiophene-2-carboxylate

A mixture of 4-cyano-5-(methylthio)thiophene-2-carboxylic acid (2.0 g, 10 mmol), benzyltrimethylamonium chloride (2.25 g, 10 mmol), tertbutyl bromide (54 mL, 480 mmol) and anhydrous potassium carbonate (36 g, 260 mmol) in dimethylacetamide (100 mL) was stirred at 60° C. for 6 hours. After cooling, the mixture was diluted with ethyl acetate (400 mL) and washed with water. Organic layer was dried and evaporated under reduced pressure to give a residue which was purified by chromatography (eluent ethyl acetate/n-hexane 3:1) thus yielding 1.5 g of the title compound.

LC-MS: Rt 7.4; $[M+H]^+$ 256.

Example 3

Tert-butyl 4-cyano-5-(methylsulfonyl)thiophene-2-carboxylate

A mixture of tert-butyl 4-cyano-5-(methylthio)thiophene-2-carboxylate (1.4 g, 5.5 mmol) and oxone (14.4 g, 21.5 mmol) in dimethylformamide (100 mL) was stirred at room temperature for 16 hours. The reaction mixture was then poured into ice/water (400 mL) and extracted with ethyl acetate. Organic layer was washed with water, dried over anhydrous sodium sulfate and evaporated to dryness to afford 1.5 g of the title compound. LC-MS: Rt 6.2; $[M+H]^+$ 288.

Example 4

Tert-butyl 4-cyano-5-hydrazinothiophene-2-carboxylate

A mixture of tert-butyl 4-cyano-5-(methylsulfonyl)thiophene-2-carboxylate (2.0 g, 7.0 mmol) and hydrazine hydrate (1.7 mL) in methyl alcohol (30 mL) was stirred at 60° C. for 2 hours. The reaction mixture was diluted with ethyl acetate (100 mL) and washed with water. Organic layer was separated, dried over anhydrous sodium sulfate and evaporated. Through chromatography purification (n-hexane/ethyl acetate 3:2), 1 g of the title compound was thus obtained.

LC-MS: Rt 5.6; $[M+H]^+$ 240.

Example 5

Tert-butyl 3-amino-1H-thieno[2,3-c]pyrazole-5-carboxylate

A mixture of tert-butyl 4-cyano-5-hydrazinothiophene-2-carboxylate (1.0 g, 4.2 mmol) and hydrochloric acid (0.7 mL of a 37% solution) in methyl alcohol (15 mL) was stirred at room temperature for 14 hours. The reaction mixture was diluted with ethyl acetate (50 mL) and washed with an aqueous solution of sodium bicarbonate. Organic layer was separated, dried over anhydrous sodium sulfate and evaporated to afford 0.9 g of the title compound.

LC-MS: Rt 4.5; $[M+H]^+$ 240.

Example 6

5-Tert-butyl 1-ethyl 3-amino-1H-thieno[2,3-c]pyrazole-1,5-dicarboxylate

A solution of ethyl chlorocarbonate (4.90 mL, 51.7 mmol) in tetrahydrofuran (THF, 60 mL) was slowly added to a mixture of tert-butyl 3-amino-1H-thieno[2,3-c]pyrazole-5-carboxylate (12.0 g, 50.2 mmol) and diisopropylethylamine (DIEA, 51.5 mL, 301 mmol) in THF (300 mL), maintaining the temperature between −5 and −10° C. The reaction was kept at the same temperature for 5 minutes then allowed to reach room temperature. The obtained mixture was evaporated to dryness under vacuum and the residue extracted with ethyl acetate (AcOEt) and water. The organic layer was separated, dried over sodium sulfate and evaporated to dryness. The resulting raw material was triturated with diethyl ether to give 13.7 g of the title compound as a white solid.

LC-MS: Rt 5.57; $[M+H]^+$ 312.

Example 7

3-(2-Nitro-benzoylamino)-thieno[2,3-c]pyrazole-1,5-dicarboxylic Acid 5-tert-butyl Ester 1-ethyl Ester

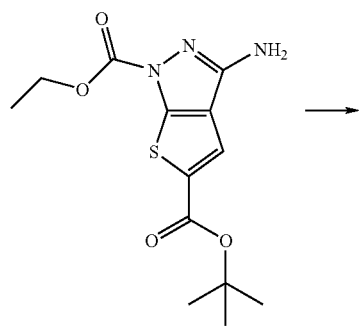

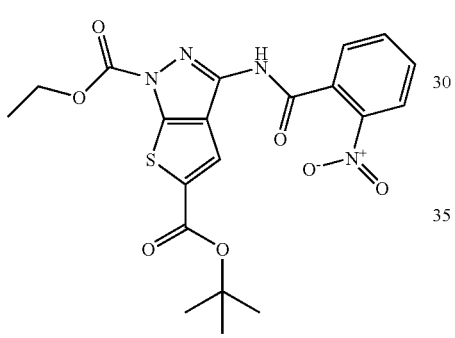

To a solution of 5-tert-butyl 1-ethyl 3-amino-1H-thieno[2,3-c]pyrazole-1,5-dicarboxylate (500 mg, 1.606 mmol) and diisopropylethylamine (DIEA, 0.824 mL, 4.818 mmol) in tetrahydrofuran (THF, 20 mL) at 0° C., 2-nitro-benzoyl chloride (0.318 mL, 2.409 mmol) was added. The reaction mixture was kept at the same temperature for 10 minutes then allowed to reach room temperature and let react overnight. The solvent was removed under vacuum, the residue was dissolved in dichloromethane (DCM) and washed with a 10% solution of acetic acid (AcOH), water, saturated NaHCO$_3$ and brine. The crude was purified on silica gel (eluant dichloromethane/methanol 96/4) yielding 512 mg (69%) of the title compound.

LC-MS: Rt 7.48; [M+H]$^+$ 461

$^1$H NMR (400 MHz, DMSO-d6) δ ppm 1.40 (d, J=7.07 Hz, 3H) 1.57 (s, 9H) 4.50 (d, J=7.07 Hz, 2H) 7.77-7.87 (m, 2H) 7.87-7.95 (m, 1H) 8.03 (s, 1H) 8.15-8.23 (m, 1H) 12.14 (s, 1H)

By operating in an analogous way and by reacting 5-tert-butyl 1-ethyl 3-amino-1H-thieno[2,3-c]pyrazole-1,5-dicarboxylate with the appropriate acyl chloride derivative, the following compounds was thus prepared:

3-[4-(4-Methyl-piperazin-1-yl)-2-nitro-benzoylamino]-thieno[2,3-c]pyrazole-1,5-dicarboxylic acid 5-tert-butyl ester 1-ethyl ester;

LC-MS: Rt 4.21; [M+H]$^+$ 559;

$^1$H NMR (400 MHz, DMSO-D6) δ ppm 1.40 (t, 3H) 1.56 (s, 9H) 2.25 (s, 3H) 2.40-2.50 (m, 4H) 3.30-3.45 (m, 4H) 4.50 (q, 2H) 7.25 (dd, 1H) 7.47 (dd, 1H) 7.69 (d, 1H) 7.96 (s, 1H) 11.93 (s, 1H).

Example 8

3-(2-Amino-benzoylamino)-thieno[2,3-c]pyrazole-1,5-dicarboxylic Acid 5-tert-butyl Ester 1-ethyl Ester

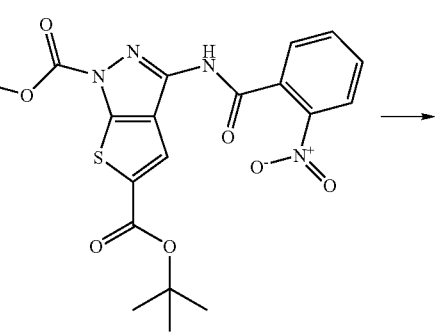

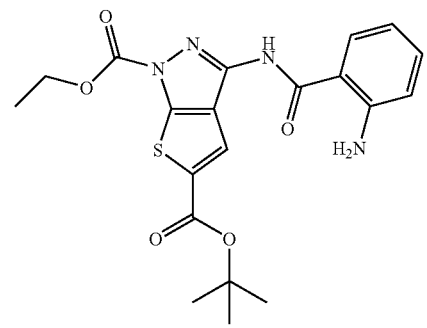

The suspension of 3-(2-Nitro-benzoylamino)-thieno[2,3-c]pyrazole-1,5-dicarboxylic acid 5-tert-butyl ester 1-ethyl ester (984 mg, 2.136 mmol) and Pd/C 10% (200 mg) in ethyl acetate (AcOEt, 35 mL) was shaken under hydrogen pressure (40 psi) for 10 hours. The solid was filtered on celite, washed with AcOEt and the filtrate was evaporated under vacuum to yield 894 mg (97%) of title compound.

LC-MS: Rt 7.9; [M+H]$^+$ 431.

By operating in an analogous way and by using 3-[4-(4-Methyl-piperazin-1-yl)-2-nitro-benzoylamino]-thieno[2,3-c]pyrazole-1,5-dicarboxylic acid 5-tert-butyl ester 1-ethyl ester as the starting material, the following compounds was thus prepared:

3-[2-Amino-4-(4-methyl-piperazin-1-yl)-benzoylamino]-thieno[2,3-c]pyrazole-1,5-dicarboxylic acid 5-tert-butyl ester 1-ethyl ester

[M+H]+ 529

Example 9

3-(2-Amino-benzoylamino)-1H-thieno[2,3-c]pyrazole-5-carboxylic Acid tert-butyl Ester

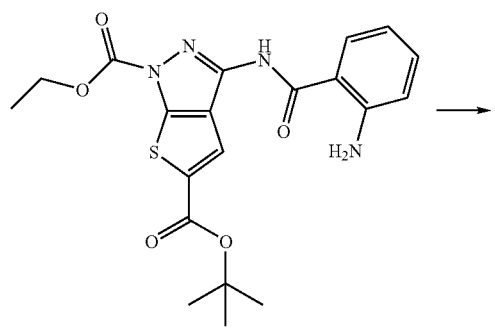

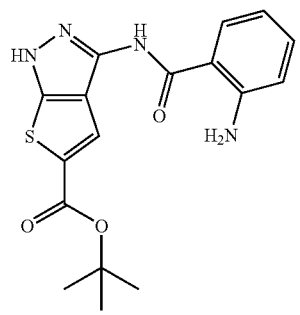

30 mg of 3-(2-Amino-benzoylamino)-thieno[2,3-c]pyrazole-1,5-dicarboxylic acid 5-tert-butyl ester 1-ethyl ester (0.058 mmol) were treated with a 10% solution of TEA and methanol (8 mL) at room temperature for 3 hours. The solvent was removed under vacuum and the residue was purified by flash chromatography (eluant dichloromethane/methanol 99/1) yielding 19 mg (91%) of the title compound.

LC-MS: Rt 6.18; [M+H]+ 359.

¹H NMR (400 MHz, DMSO-D6) δ ppm 1.54 (s, 9H) 6.45-6.54 (m, 1H) 6.73-6.87 (m, 2H) 7.69-7.80 (m, 1H) 7.92 (s, 1H) 10.83 (s, 1H) 12.93 (s, 1H)

By operating in an analogous way and by using 3-[2-Amino-4-(4-methyl-piperazin-1-yl)-benzoylamino]-thieno[2,3-c]pyrazole-1,5-dicarboxylic acid 5-tert-butyl ester 1-ethyl ester as the starting material, the following compounds was thus prepared:

3-[2-Amino-4-(4-methyl-piperazin-1-yl)-benzoylamino]-1H-thieno[2,3-c]pyrazole-5-carboxylic acid tert-butyl ester.

[M+H]+ 457;

¹H NMR (400 MHz, DMSO-d6) δ ppm 1.53 (s, 9H) 2.28 (s, 3H) 2.43-2.59 (m, 4H) 3.17-3.28 (m, 4H) 6.13-6.31 (m, 2H) 6.57 (br. s., 2H) 7.68 (d, J=9.02 Hz, 1H) 7.90 (s, 1H) 10.49 (br. s., 1H) 12.87 (br. s., 1H)

Example 10

3-{2-[(1H-Pyrrole-2-carbonyl)-amino]-benzoylamino}-thieno[2,3-c]pyrazole-1,5-dicarboxylic Acid 5-tert-butyl Ester 1-ethyl Ester

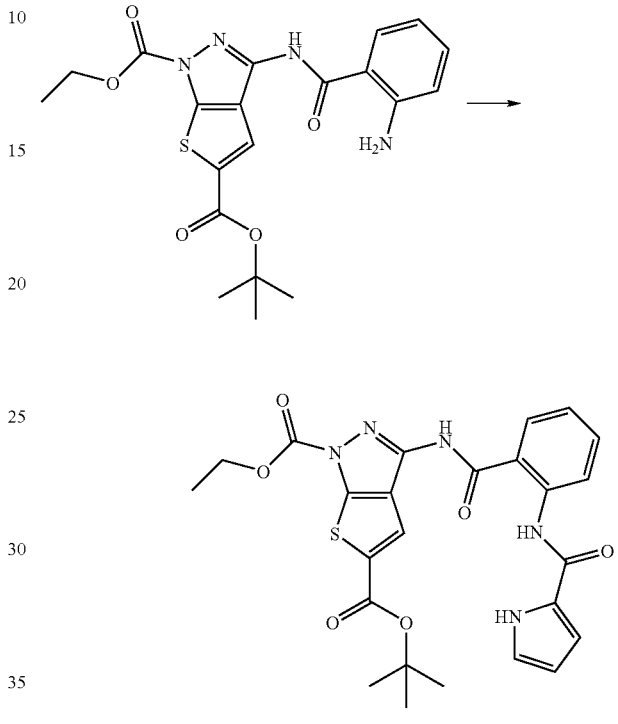

To a suspension of pyrrole-2-carboxilic acid (1 g, 9 mmol) in toluene (7 ml) oxalyl chloride (2.28 mL, 27 mmol) and a catalytic amount of DMF were added. After 4 hours the reaction was complete. The solvent was removed under vacuum and the residue was stripped twice with toluene. The acyl chloride was isolated as brownish solid (1.086 g, 93%).

To the solution of 3-(2-amino-benzoylamino)-thieno[2,3-c]pyrazole-1,5-dicarboxylic acid 5-tert-butyl ester 1-ethyl ester (600 mg, 1.393 mmol) and DIEA (0.595 mL, 3.482 mmol) in DCM (15 mL) at 0° C., pyrrole-2-carbonyl chloride (361 mg, 2.786 mmol) was added portionwise under stirring. The mixture was allowed to reach room temperature. After 3.5 hours the mixture was diluted with DCM (30 mL) and washed with water (2×50 mL), dried over Na₂SO₄ and evaporated under vacuum. Treatment with DCM and methanol afforded the product as white solid. The filtrate was purified over silica gel (eluant dichloromethane/methanol 95/5) yielding 460 mg (63%) of the product.

LC-MS: Rt 8.33; [M+H]+ 524;

By operating in an analogous way and by reacting 3-(2-amino-benzoylamino)-thieno[2,3-c]pyrazole-1,5-dicarboxylic acid 5-tert-butyl ester 1-ethyl ester with the appropriate acyl chloride derivative, the following compounds were thus prepared:

3-{2-[(5-Methyl-isoxazole-4-carbonyl)-amino]-benzoylamino}-thieno[2,3-c]pyrazole-1,5-dicarboxylic acid 5-tert-butyl ester 1-ethyl ester, [M+H]+ 540;

3-{2-[(Tetrahydro-pyran-4-carbonyl)-amino]-benzoylamino}-thieno[2,3-c]pyrazole-1,5-dicarboxylic acid 5-tert-butyl ester 1-ethyl ester, [M+H]+ 543;

3-{2-[(5-Methyl-1H-pyrazole-3-carbonyl)-amino]-benzoylamino}-thieno[2,3-c]pyrazole-1,5-dicarboxylic acid 5-tert-butyl ester 1-ethyl ester, [M+H]+ 539;

3-{2-[(Furan-2-carbonyl)-amino]-benzoylamino}-thieno[2,3-c]pyrazole-1,5-dicarboxylic acid 5-tert-butyl ester 1-ethyl ester, [M+H]+ 525;

3-{2-[(2-Ethyl-5-methyl-2H-pyrazole-3-carbonyl)-amino]-benzoylamino}-thieno[2,3-c]pyrazole-1,5-dicarboxylic acid 5-tert-butyl ester 1-ethyl ester, [M+H]+ 567;

By operating in an analogous way and by reacting 3-[2-Amino-4-(4-methyl-piperazin-1-yl)-benzoylamino]-thieno[2,3-c]pyrazole-1,5-dicarboxylic acid 5-tert-butyl ester 1-ethyl ester with the appropriate acyl chloride derivative, the following compounds were thus prepared:

3-{4-(4-Methyl-piperazin-1-yl)-2-[(1H-pyrrole-2-carbonyl)-amino]-benzoylamino}-thieno[2,3-c]pyrazole-1,5-dicarboxylic acid 5-tert-butyl ester 1-ethyl ester, [M+H]+ 622;

3-[2-[(5-Methyl-isoxazole-4-carbonyl)-amino]-4-(4-methyl-piperazin-1-yl)-benzoylamino]-thieno[2,3-c]pyrazole-1,5-dicarboxylic acid 5-tert-butyl ester 1-ethyl ester, [M+H]+ 638;

3-{4-(4-Methyl-piperazin-1-yl)-2-[(tetrahydro-pyran-4-carbonyl)-amino]-benzoylamino}-thieno[2,3-c]pyrazole-1,5-dicarboxylic acid 5-tert-butyl ester 1-ethyl ester, [M+H]+ 641;

3-{4-(4-Methyl-piperazin-1-yl)-2-[(5-methyl-1H-pyrazole-3-carbonyl)-amino]-benzoylamino}-thieno[2,3-c]pyrazole-1,5-dicarboxylic acid 5-tert-butyl ester 1-ethyl ester, [M+H]+ 637;

3-[2-[(Furan-2-carbonyl)-amino]-4-(4-methyl-piperazin-1-yl)-benzoylamino]-thieno[2,3-c]pyrazole-1,5-dicarboxylic acid 5-tert-butyl ester 1-ethyl ester, [M+H]+ 623;

3-[2-[(2-Ethyl-5-methyl-2H-pyrazole-3-carbonyl)-amino]-4-(4-methyl-piperazin-1-yl)-benzoylamino]-thieno[2,3-c]pyrazole-1,5-dicarboxylic acid 5-tert-butyl ester 1-ethyl ester, [M+H]+ 665.

Example 11

3-{2-[(1H-Pyrrole-2-carbonyl)-amino]-benzoylamino}-1H-thieno[2,3-c]pyrazole-5-carboxylic Acid tert-butyl Ester

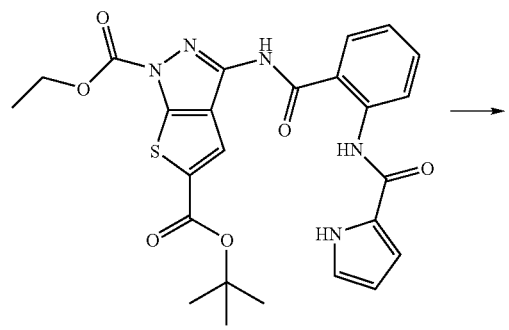

-continued

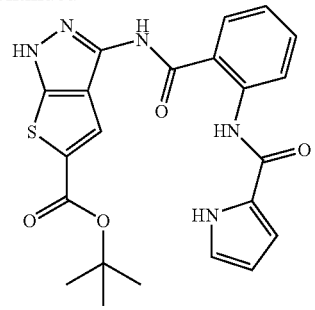

3-{2-[(1H-Pyrrole-2-carbonyl)-amino]-benzoylamino}-thieno[2,3-c]pyrazole-1,5-dicarboxylic acid 5-tert-butyl ester 1-ethyl ester (32 mg, 0.061 mmol) were treated with 20 mL of a 10% solution of TEA/methanol for 2 hours at room temperature. After removal of the solvent the crude was purified on silica gel (eluant dichloromethane/methanol 97/3) to yield 25 mg (90%) of the title compound.

LC-MS: Rt 6.8; [M+H]+ 452.

$^1$H NMR (400 MHz, DMSO-D6) δ ppm 1.56 (s, 9H) 6.14-6.25 (m, 1H) 6.76-6.84 (m, 1H) 6.99-7.09 (m, 1H) 7.16-7.26 (m, 1H) 7.55-7.69 (m, 1H) 7.99 (s, 1H) 8.01-8.09 (m, 1H) 8.50-8.59 (m, 1H) 11.43 (s, 1H) 11.60-11.69 (m, 1H) 11.80-11.91 (m, 1H) 13.08 (s, 1H).

Example 12

3-{2-[(1H-Pyrrole-2-carbonyl)-amino]-benzoylamino}-thieno[2,3-c]pyrazole-1,5-dicarboxylic Acid 1-ethyl Ester

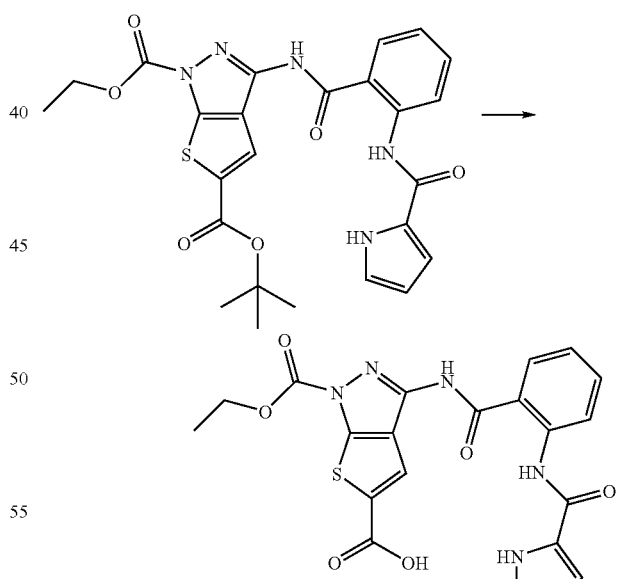

The solution of 3-{2-[(1H-Pyrrole-2-carbonyl)-amino]-benzoylamino}-thieno[2,3-c]pyrazole-1,5-dicarboxylic acid 5-tert-butyl ester 1-ethyl ester (460.8 mg, 0.88 mmol) in dioxane (10 mL) was treated with HCl 4M in dioxane (10 mL) overnight, the solvent was then removed and the residue was triturated with diethylether (Et$_2$O, 15 mL) yielding 397 mg (96%) of the product, LC-MS: Rt 3.7; [M+H]+ 468;

By operating as above reported and by starting from the suitable intermediate derivative, the following compounds were analogously prepared:

3-{2-[(5-Methyl-isoxazole-4-carbonyl)-amino]-benzoylamino}-thieno[2,3-c]pyrazole-1,5-dicarboxylic acid 1-ethyl ester, [M+H]⁺ 484;

3-{2-[(Tetrahydro-pyran-4-carbonyl)-amino]-benzoylamino}-thieno[2,3-c]pyrazole-1,5-dicarboxylic acid 1-ethyl ester, [M+H]⁺ 487;

3-{2-[(5-Methyl-1H-pyrazole-3-carbonyl)-amino]-benzoylamino}-thieno[2,3-c]pyrazole-1,5-dicarboxylic acid 1-ethyl ester, [M+H]⁺ 483;

3-{2-[(Furan-2-carbonyl)-amino]-benzoylamino}-thieno[2,3-c]pyrazole-1,5-dicarboxylic acid 1-ethyl ester, [M+H]⁺ 469;

3-{2-[(2-Ethyl-5-methyl-2H-pyrazole-3-carbonyl)-amino]-benzoylamino}-thieno[2,3-c]pyrazole-1,5-dicarboxylic acid 1-ethyl ester, [M+H]⁺ 511;

3-{4-(4-Methyl-piperazin-1-yl)-2-[(1H-pyrrole-2-carbonyl)-amino]-benzoylamino}-thieno[2,3-c]pyrazole-1,5-dicarboxylic acid 1-ethyl ester, [M+H]⁺ 566;

3-[2-[(5-Methyl-isoxazole-4-carbonyl)-amino]-4-(4-methyl-piperazin-1-yl)-benzoylamino]-thieno[2,3-c]pyrazole-1,5-dicarboxylic acid 1-ethyl ester, [M+H]⁺ 582;

3-{4-(4-Methyl-piperazin-1-yl)-2-[(tetrahydro-pyran-4-carbonyl)-amino]-benzoylamino}-thieno[2,3-c]pyrazole-1,5-dicarboxylic acid 1-ethyl ester, [M+H]⁺ 585;

3-{4-(4-Methyl-piperazin-1-yl)-2-[(5-methyl-1H-pyrazole-3-carbonyl)-amino]-benzoylamino}-thieno[2,3-c]pyrazole-1,5-dicarboxylic acid 1-ethyl ester, [M+H]⁺ 581;

3-[2-[(Furan-2-carbonyl)-amino]-4-(4-methyl-piperazin-1-yl)-benzoylamino]-thieno[2,3-c]pyrazole-1,5-dicarboxylic acid 1-ethyl ester, [M+H]⁺ 567 and 3-[2-[(2-Ethyl-5-methyl-2H-pyrazole-3-carbonyl)-amino]-4-(4-methyl-piperazin-1-yl)-benzoylamino]-thieno[2,3-c]pyrazole-1,5-dicarboxylic acid 1-ethyl ester, [M+H]⁺ 609.

Example 13

5-(1-Methyl-1-phenyl-ethylcarbamoyl)-3-{2-[(1H-pyrrole-2-carbonyl)amino]benzoylamino}-thieno[2,3-c]pyrazole-1-carboxylic Acid ethyl Ester

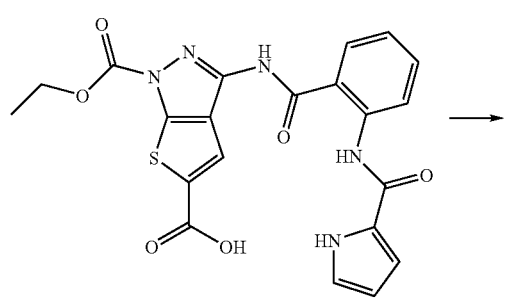

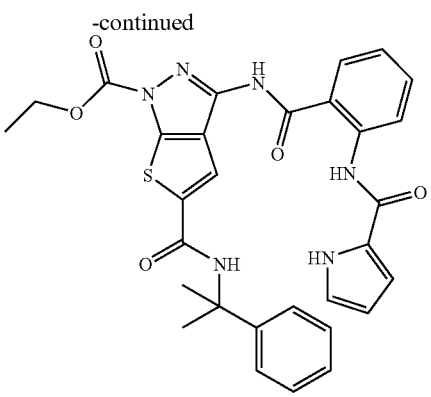

A mixture of 3-{2-[(1H-Pyrrole-2-carbonyl)-amino]-benzoylamino}-thieno[2,3-c]pyrazole-1,5-dicarboxylic acid 1-ethyl ester (198.5 mg, 0.4246 mmol), 2-(1H-benzotriazol-1-yl)-1,1,3,3-tetramethyluronium tetrafluoroborate (TBTU, 204 mg, 0.6369 mmol), DIEA (0.29 mL, 1.6984 mmol) and cumylamine (115 mg, 0.8492 mmol) in DMF (10 mL) was stirred at room temperature. After 2 hours the mixture was diluted with AcOEt (40 mL) and washed with saturated NaHCO₃, water and brine. The organic layer was dried over Na₂SO₄ and evaporated to give 495 mg of crude that was used in the next step without further purification, LC-MS: Rt 7.36; [M+H]⁺ 585.

By operating as above reported and by starting from the suitable intermediate derivative, the following compounds were analogously prepared:

3-{2-[(5-Methyl-isoxazole-4-carbonyl)-amino]-benzoylamino}-5-(1-methyl-1-phenyl-ethylcarbamoyl)-thieno[2,3-c]pyrazole-1-carboxylic acid ethyl ester, [M+H]⁺ 601;

5-(1-Methyl-1-phenyl-ethylcarbamoyl)-3-{2-[(tetrahydro-pyran-4-carbonyl)-amino]-benzoylamino}-thieno[2,3-c]pyrazole-1-carboxylic acid ethyl ester, [M+H]⁺ 604;

5-(1-Methyl-1-phenyl-ethylcarbamoyl)-3-{2-[(5-methyl-1H-pyrazole-3-carbonyl)-amino]-benzoylamino}-thieno[2,3-c]pyrazole-1-carboxylic acid ethyl ester, [M+H]⁺ 600;

3-{2-[(Furan-2-carbonyl)-amino]-benzoylamino}-5-(1-methyl-1-phenyl-ethylcarbamoyl)-thieno[2,3-c]pyrazole-1-carboxylic acid ethyl ester, [M+H]⁺ 586;

3-{2-[(2-Ethyl-5-methyl-2H-pyrazole-3-carbonyl)-amino]-benzoylamino}-5-(1-methyl-1-phenyl-ethylcarbamoyl)-thieno[2,3-c]pyrazole-1-carboxylic acid ethyl ester, [M+H]⁺ 628;

5-(1-Methyl-1-phenyl-ethylcarbamoyl)-3-{4-(4-methyl-piperazin-1-yl)-2-[(1H-pyrrole-2-carbonyl)-amino]-benzoylamino}-thieno[2,3-c]pyrazole-1-carboxylic acid ethyl ester, [M+H]⁺ 683;

3-[2-[(5-Methyl-isoxazole-4-carbonyl)-amino]-4-(4-methyl-piperazin-1-yl)-benzoylamino]-5-(1-methyl-1-phenyl-ethylcarbamoyl)-thieno[2,3-c]pyrazole-1-carboxylic acid ethyl ester, [M+H]⁺ 699;

5-(1-Methyl-1-phenyl-ethylcarbamoyl)-3-{4-(4-methyl-piperazin-1-yl)-2-[(tetrahydro-pyran-4-carbonyl)-amino]-benzoylamino}-thieno[2,3-c]pyrazole-1-carboxylic acid ethyl ester, [M+H]⁺ 702;

5-(1-Methyl-1-phenyl-ethylcarbamoyl)-3-{4-(4-methyl-piperazin-1-yl)-2-[(5-methyl-1H-pyrazole-3-carbonyl)-amino]-benzoylamino}-thieno[2,3-c]pyrazole-1-carboxylic acid ethyl ester, [M+H]+ 698;

3-[2-[(Furan-2-carbonyl)-amino]-4-(4-methyl-piperazin-1-yl)-benzoylamino]-5-(1-methyl-1-phenyl-ethylcarbamoyl)-thieno[2,3-c]pyrazole-1-carboxylic acid ethyl ester, [M+H]+ 684;

3-[2-[(2-Ethyl-5-methyl-2H-pyrazole-3-carbonyl)-amino]-4-(4-methyl-piperazin-1-yl)-benzoylamino]-5-(1-methyl-1-phenyl-ethylcarbamoyl)-thieno[2,3-c]pyrazole-1-carboxylic acid ethyl ester, [M+H]+ 726;

5-[1-(2-Fluoro-phenyl)-1-methyl-ethylcarbamoyl]-3-{2-[(1H-pyrrole-2-carbonyl)amino]-benzoylamino}-thieno[2,3-c]pyrazole-1-carboxylic acid ethyl ester, LC-MS: Rt 7.38, [M+H]+ 603;

5-[1-(2-Fluoro-phenyl)-1-methyl-ethylcarbamoyl]-3-{2-[(5-methyl-isoxazole-4-carbonyl)-amino]-benzoylamino}-thieno[2,3-c]pyrazole-1-carboxylic acid ethyl ester, [M+H]+ 619;

5-[1-(2-Fluoro-phenyl)-1-methyl-ethylcarbamoyl]-3-{2-[(tetrahydro-pyran-4-carbonyl)-amino]-benzoylamino}-thieno[2,3-c]pyrazole-1-carboxylic acid ethyl ester, [M+H]+ 622;

5-[1-(2-Fluoro-phenyl)-1-methyl-ethylcarbamoyl]-3-{2-[(5-methyl-1H-pyrazole-3-carbonyl)-amino]-benzoylamino}-thieno[2,3-c]pyrazole-1-carboxylic acid ethyl ester, [M+H]+ 618;

5-[1-(2-Fluoro-phenyl)-1-methyl-ethylcarbamoyl]-3-{2-[(furan-2-carbonyl)-amino]-benzoylamino}-thieno[2,3-c]pyrazole-1-carboxylic acid ethyl ester, [M+H]+ 604;

3-{2-[(2-Ethyl-5-methyl-2H-pyrazole-3-carbonyl)-amino]-benzoylamino}-5-[1-(2-fluoro-phenyl)-1-methyl-ethylcarbamoyl]-thieno[2,3-c]pyrazole-1-carboxylic acid ethyl ester, [M+H]+ 646;

5-[1-(2-Fluoro-phenyl)-1-methyl-ethylcarbamoyl]-3-{4-(4-methyl-piperazin-1-yl)-2-[(1H-pyrrole-2-carbonyl)-amino]-benzoylamino}-thieno[2,3-c]pyrazole-1-carboxylic acid ethyl ester, [M+H]+ 701;

5-[1-(2-Fluoro-phenyl)-1-methyl-ethylcarbamoyl]-3-[2-[(5-methyl-isoxazole-4-carbonyl)-amino]-4-(4-methyl-piperazin-1-yl)-benzoylamino]-thieno[2,3-c]pyrazole-1-carboxylic acid ethyl ester, [M+H]+ 717;

5-[1-(2-Fluoro-phenyl)-1-methyl-ethylcarbamoyl]-3-{4-(4-methyl-piperazin-1-yl)-2-[(tetrahydro-pyran-4-carbonyl)-amino]-benzoylamino}-thieno[2,3-c]pyrazole-1-carboxylic acid ethyl ester, [M+H]+ 720;

5-[1-(2-Fluoro-phenyl)-1-methyl-ethylcarbamoyl]-3-{4-(4-methyl-piperazin-1-yl)-2-[(5-methyl-1H-pyrazole-3-carbonyl)-amino]-benzoylamino}-thieno[2,3-c]pyrazole-1-carboxylic acid ethyl ester, [M+H]+ 716;

5-[1-(2-Fluoro-phenyl)-1-methyl-ethylcarbamoyl]-3-[2-[(furan-2-carbonyl)-amino]-4-(4-methyl-piperazin-1-yl)-benzoylamino]-thieno[2,3-c]pyrazole-1-carboxylic acid ethyl ester, [M+H]+ 702 and 3-[2-[(2-Ethyl-5-methyl-2H-pyrazole-3-carbonyl)-amino]-4-(4-methyl-piperazin-1-yl)-benzoylamino]-5-[1-(2-fluoro-phenyl)-1-methyl-ethylcarbamoyl]-thieno[2,3-c]pyrazole-1-carboxylic acid ethyl ester, [M+H]+ 744.

Example 14

3-[2-[(1H-Pyrrole-2-carbonyl)-amino]-benzoylamino]-1H-thieno[2,3-c]pyrazole-5-carboxylic Acid (1-methyl-1-phenyl-ethyl)-amide

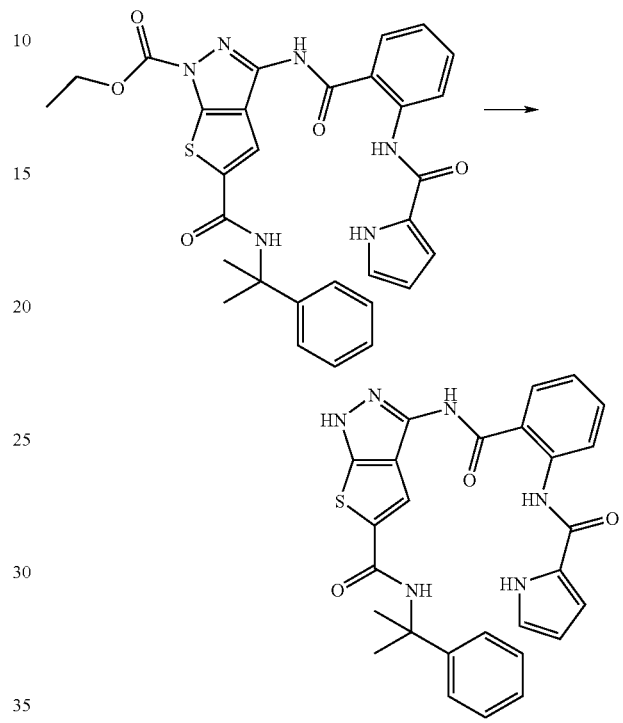

5-(1-Methyl-1-phenyl-ethylcarbamoyl)-3-{2-[(1H-pyrrole-2-carbonyl)amino]benzoylamino}-thieno[2,3-c]pyrazole-1-carboxylic acid ethyl ester as crude from the previous reaction was treated with a 10% solution of TEA in methanol (25 mL) overnight. The solvent was evaporated under vacuum and the product was purified by flash chromatography (eluant dichloromethane/methanol 97/3) (78.5 mg, 36%), LC-MS: Rt 6.26; [M+H]+ 513, $^1$H NMR (400 MHz, DMSO-D6) δ ppm 1.68 (s, 6H) 6.13-6.23 (m, 1H) 6.85-6.97 (m, 1H) 6.98-7.06 (m, 1H) 7.15-7.26 (m, J=7.19 Hz, 2H) 7.26-7.36 (m, 2H) 7.36-7.45 (m, 2H) 7.57-7.69 (m, 1H) 8.01-8.12 (m, 1H) 8.18 (s, 1H) 8.56-8.61 (m, 1H) 8.63 (s, 1H) 11.33 (s, 1H) 11.69-11.81 (m, 1H) 11.80-11.89 (m, 1H).

By operating as above reported and by starting from the suitable intermediate, the following compounds were analogously prepared:

3-{2-[(1H-Pyrrole-2-carbonyl)-amino]-benzoylamino}-1H-thieno[2,3-c]pyrazole-5-carboxylic acid [1-(2-fluoro-phenyl)-1-methyl-ethyl]-amide, LC-MS: Rt 6.27; [M+H]+ 531, $^1$H NMR (400 MHz, DMSO-D6) δ ppm 1.64-1.86 (m, 6H) 6.12-6.24 (m, 1H) 6.87-6.96 (m, 1H) 6.98-7.03 (m, 1H) 7.05-7.23 (m, 3H) 7.23-7.34 (m, 1H) 7.35-7.44 (m, 1H) 7.54-7.64 (m, 1H) 8.05-8.11 (m, 1H) 8.14 (s, 1H) 8.55-8.67 (m, 2H) 11.43 (none, 1H) 11.81 (s, 3H) 13.01 (br. s, 1H);

3-[2-((E)-2-Cyano-3-hydroxy-but-2-enoylamino)-benzoylamino]-1H-thieno[2,3-c]pyrazole-5-carboxylic acid (1-methyl-1-phenyl-ethyl)-amide, [M+H]+ 529, ¹H NMR (400 MHz, DMSO-d6) δ ppm 1.66 (s, 6H) 1.94 (s, 3H) 6.92-7.06 (m, 1H) 7.11-7.20 (m, 1H) 7.24-7.32 (m, 2H) 7.32-7.43 (m, 3H) 7.43-7.52 (m, 1H) 8.21 (s, 1H) 8.25-8.36 (m, 1H) 8.48 (br. s., 1H) 10.94 (br. s., 1H) 12.05 (br. s., 1H) 12.71 (br. s., 1H);

3-{2-[(Tetrahydro-pyran-4-carbonyl)-amino]-benzoylamino}-1H-thieno[2,3-c]pyrazole-5-carboxylic acid (1-methyl-1-phenyl-ethyl)-amide, [M+H]⁺ 532, ¹H NMR (400 MHz, DMSO-d6) δ ppm 1.59-1.75 (m, 8H) 1.77-1.87 (m, 2H) 2.59-2.73 (m, 1H) 3.36-3.44 (m, 2H) 3.83-3.94 (m, 2H) 7.14-7.27 (m, 2H) 7.27-7.34 (m, 2H) 7.35-7.43 (m, 2H) 7.53-7.62 (m, 1H) 7.89-7.99 (m, 1H) 8.15 (s, 1H) 8.30-8.37 (m, 1H) 8.61 (br. s., 1H) 10.89 (br. s., 1H) 11.23 (br. s., 1H) 12.92 (br. s., 1H);

3-{2-[(5-Methyl-1H-pyrazole-3-carbonyl)-amino]-benzoylamino}-1H-thieno[2,3-c]pyrazole-5-carboxylic acid (1-methyl-1-phenyl-ethyl)-amide, [M+H]⁺ 528; 3-{2-[(Furan-2-carbonyl)-amino]-benzoylamino}-1H-thieno[2,3-c]pyrazole-5-carboxylic acid (1-methyl-1-phenyl-ethyl)-amide, [M+H]⁺ 514;

¹H NMR (400 MHz, DMSO-d6) δ ppm 1.66 (s, 6H) 6.70 (dd, J=3.54, 1.71 Hz, 1H) 7.12-7.22 (m, 1H) 7.22-7.34 (m, 4H) 7.33-7.41 (m, 2H) 7.57-7.67 (m, 1H) 7.89-7.97 (m, 1H) 7.99-8.07 (m, 1H) 8.09 (s, 1H) 8.49-8.65 (m, 2H) 11.35 (br. s., 1H) 11.83 (br. s., 1H) 12.98 (br. s., 1H);

3-{2-[(Furan-3-carbonyl)-amino]-benzoylamino}-1H-thieno[2,3-c]pyrazole-5-carboxylic acid (1-methyl-1-phenyl-ethyl)-amide, [M+H]⁺ 514, ¹H NMR (400 MHz, DMSO-d6) δ ppm 1.66 (s, 6H) 6.88-6.93 (m, 1H) 7.13-7.21 (m, 1H) 7.23-7.32 (m, 3H) 7.34-7.41 (m, 2H) 7.56-7.68 (m, 1H) 7.77-7.82 (m, 1H) 8.01-8.09 (m, 1H) 8.15 (br. s., 1H) 8.39-8.41 (m, 1H) 8.42-8.50 (m, 1H) 8.57 (s, 1H) 11.32 (br. s., 1H) 11.58 (br. s., 1H) 12.94 (br. s., 1H);

3-{2-[(2-Ethyl-5-methyl-2H-pyrazole-3-carbonyl)-amino]-benzoylamino}-1H-thieno[2,3-c]pyrazole-5-carboxylic acid (1-methyl-1-phenyl-ethyl)-amide, [M+H]⁺ 556, ¹H NMR (400 MHz, DMSO-d6) δ ppm 1.32 (t, J=7.19 Hz, 1H) 1.67 (s, 6H) 2.21 (s, 3H) 4.46 (q, J=7.07 Hz, 2H) 6.74 (s, 1H) 7.14-7.22 (m, 1H) 7.24-7.34 (m, 3H) 7.34-7.42 (m, 2H) 7.59-7.70 (m, 1H) 8.02-8.10 (m, 1H) 8.19 (s, 1H) 8.43-8.51 (m, 1H) 8.64 (br. s., 1H) 11.33 (br. s., 1H) 12.95 (br. s., 1H);

3-(2-Isobutyrylamino-benzoylamino)-1H-thieno[2,3-c]pyrazole-5-carboxylic acid (1-methyl-1-phenyl-ethyl)-amide, [M+H]⁺ 490, ¹H NMR (400 MHz, DMSO-d6) δ ppm 1.15 (d, 6H) 1.67 (s, 6H) 2.54-2.67 (m, 1H) 7.14-7.26 (m, 2H) 7.26-7.34 (m, 2H) 7.34-7.43 (m, 2H) 7.52-7.63 (m, 1H) 7.87-7.98 (m, 1H) 8.11 (br. s., 1H) 8.27-8.35 (m, 1H) 8.57 (s, 1H) 10.78 (br. s., 1H) 11.20 (br. s., 1H) 12.90 (br. s., 1H);

3-{2-[(2-Methyl-2H-pyrazole-3-carbonyl)-amino]-benzoylamino}-1H-thieno[2,3-c]pyrazole-5-carboxylic acid (1-methyl-1-phenyl-ethyl)-amide, [M+H]⁺ 528, ¹H NMR (400 MHz, DMSO-d6) δ ppm 1.65 (s, 6H) 4.10 (s, 3H) 6.97 (s, 1H) 7.13-7.21 (m, 1H) 7.25-7.33 (m, 3H) 7.34-7.40 (m, 2H) 7.50 (m, 1H) 7.59-7.70 (m, 1H) 7.99-8.09 (m, 1H) 8.13 (br. s., 1H) 8.35-8.48 (m, 1H) 8.57 (s, 1H) 11.33 (br. s., 1H) 11.78 (br. s., 1H) 12.92 (br. s., 1H);

3-{2-[(1-Methyl-1H-pyrazole-3-carbonyl)-amino]-benzoylamino}-1H-thieno[2,3-c]pyrazole-5-carboxylic acid (1-methyl-1-phenyl-ethyl)-amide, [M+H]⁺ 528, ¹H NMR (400 MHz, DMSO-d6) δ ppm 1.65 (s, 6H) 3.93 (s, 3H) 6.76 (d, J=2.32 Hz, 1H) 7.14-7.20 (m, 1H) 7.20-7.33 (m, 3H) 7.34-7.39 (m, 2H) 7.57-7.65 (m, 1H) 7.84 (d, J=2.32 Hz, 1H) 7.91-8.01 (m, 1H) 8.12 (br. s., 1H) 8.59-8.66 (m, 2H) 11.28 (br. s., 1H) 11.66 (s, 1H) 12.93 (br. s., 1H);

3-{2-[(1-Methyl-1H-pyrrole-2-carbonyl)-amino]-benzoylamino}-1H-thieno[2,3-c]pyrazole-5-carboxylic acid (1-methyl-1-phenyl-ethyl)-amide, [M+H]⁺ 527, ¹H NMR (400 MHz, DMSO-d6) δ ppm 1.66 (s, 6H) 3.91 (s, 3H) 6.06-6.12 (m, 1H) 6.89-6.95 (m, 1H) 7.02-7.08 (m, 1H) 7.12-7.25 (m, 2H) 7.25-7.33 (m, 2H) 7.33-7.42 (m, 2H) 7.54-7.66 (m, 1H) 7.99-8.08 (m, 1H) 8.13 (br. s., 1H) 8.49-8.66 (m, 2H) 11.31 (br. s., 1H) 11.69 (br. s., 1H) 12.94 (br. s., 1H);

3-{2-[(Thiazole-4-carbonyl)-amino]-benzoylamino}-1H-thieno[2,3-c]pyrazole-5-carboxylic acid (1-methyl-1-phenyl-ethyl)-amide, [M+H]⁺ 531, ¹H NMR (400 MHz, DMSO-d6) δ ppm 1.65 (s, 6H) 7.14-7.21 (m, 1H) 7.25-7.32 (m, 3H) 7.34-7.40 (m, 2H) 7.61-7.68 (m, 1H) 7.94-7.99 (m, 1H) 8.06 (br. s., 1H) 8.54 (d, J=1.95 Hz, 1H) 8.57 (s, 1H) 8.64-8.70 (m, 1H) 9.22 (d, 1H) 11.31 (br. s., 1H) 12.06 (s, 1H) 12.92 (br. s., 1H);

3-{2-[(1H-Pyrrole-3-carbonyl)-amino]-benzoylamino}-1H-thieno[2,3-c]pyrazole-5-carboxylic acid (1-methyl-1-phenyl-ethyl)-amide, [M+H]⁺ 513, ¹H NMR (400 MHz, DMSO-d6) δ ppm 1.66 (s, 6H) 6.51-6.57 (m, 1H) 6.79-6.85 (m, 1H) 7.12-7.22 (m, 2H) 7.24-7.32 (m, 2H) 7.34-7.40 (m, 2H) 7.40-7.43 (m, 1H) 7.53-7.64 (m, 1H) 7.98-8.06 (m, 1H) 8.14 (s, 1H) 8.56-8.67 (m, 2H) 11.27 (s, 1H) 11.36 (br. s., 1H) 11.52 (s, 1H) 12.94 (s, 1H);

3-{2-[(1H-Imidazole-2-carbonyl)-amino]-benzoylamino}-1H-thieno[2,3-c]pyrazole-5-carboxylic acid (1-methyl-1-phenyl-ethyl)-amide, [M+H]⁺ 514, ¹H NMR (400 MHz, DMSO-d6) δ ppm 1.67 (s, 6H) 7.11-7.15 (m, 1H) 7.15-7.22 (m, 1H) 7.24-7.35 (m, 3H) 7.35-7.42 (m, 3H) 7.59-7.72 (m, 1H) 7.91-8.02 (m, 1H) 8.09 (s, 1H) 8.57-8.69 (m, 2H) 11.31 (s, 1H) 11.91 (s, 1H) 12.93 (s, 1H) 13.32 (br. s., 1H);

3-(2-Benzoylamino-benzoylamino)-1H-thieno[2,3-c]pyrazole-5-carboxylic acid (1-methyl-1-phenyl-ethyl)-amide, [M+H]⁺ 524, ¹H NMR (400 MHz, DMSO-d6) δ ppm 1.67 (s, 6H) 7.14-7.24 (m, 1H) 7.26-7.35 (m, 3H) 7.35-7.42 (m, 2H) 7.54-7.73 (m, 5H) 7.96-8.03 (m, 2H) 8.04-8.12 (m, 1H) 8.16 (br. s., 1H) 8.60 (s, 1H) 11.36 (br. s., 1H) 11.98 (br. s., 1H) 12.95 (s, 1H);

3-{2-[(1-Methyl-1H-imidazole-2-carbonyl)-amino]-benzoylamino}-1H-thieno[2,3-c]pyrazole-5-carboxylic acid (1-methyl-1-phenyl-ethyl)-amide, [M+H]⁺ 528, ¹H NMR (400 MHz, DMSO-d6) δ ppm 1.67 (s, 6H) 4.02 (s, 3H) 7.07-7.08 (m, J=0.98 Hz, 1H) 7.15-7.21 (m, 1H) 7.24-7.33 (m, 3H) 7.36-7.41 (m, 2H) 7.45 (d, J=0.61 Hz, 1H) 7.58-7.68 (m, 1H) 7.91-8.00 (m, 1H) 8.07 (br. s., 1H) 8.54-8.66 (m, 2H) 11.31 (br. s., 1H) 11.94 (s, 1H) 12.93 (br. s., 1H);

3-(2-Phenylacetylamino-benzoylamino)-1H-thieno[2,3-c]pyrazole-5-carboxylic acid (1-methyl-1-phenyl-ethyl)-amide, [M+H]⁺ 538, ¹H NMR (400 MHz, DMSO-d6) δ ppm 1.68 (s, 6H) 3.76 (s, 2H) 7.15-7.26 (m, 3H) 7.26-7.34 (m, 4H) 7.35-7.44 (m, 4H) 7.52-7.59 (m, 1H) 7.86-7.93 (m, 1H) 8.18 (s, 1H) 8.22-8.29 (m, 1H) 8.63 (s, 1H) 10.80 (s, 1H) 11.23 (s, 1H) 12.90 (s, 1H);

3-{2-[(Thiophene-2-carbonyl)-amino]-benzoylamino}-1H-thieno[2,3-c]pyrazole-5-carboxylic acid (1-methyl-1-phenyl-ethyl)-amide, [M+H]⁺ 530, ¹H NMR (400 MHz, DMSO-d6) δ ppm 1.67 (s, 6H) 7.16-7.21 (m, 1H) 7.21-7.23 (m, 1H) 7.26-7.33 (m, 3H) 7.36-7.42 (m, 2H) 7.65 (t, J=8.17 Hz, 1H) 7.86 (d, J=3.78 Hz, 1H) 7.90 (dd, J=4.94, 0.91 Hz, 1H) 8.08 (d, J=7.93 Hz, 1H) 8.18 (s, 1H) 8.49 (d, J=8.17 Hz, 1H) 8.61 (s, 1H) 11.37 (s, 1H) 12.00 (br. s., 1H) 12.95 (s, 1H);

3-{2-[(Thiophene-3-carbonyl)-amino]-benzoylamino}-1H-thieno[2,3-c]pyrazole-5-carboxylic acid (1-methyl-1-phenyl-ethyl)-amide, [M+H]⁺ 530, ¹H NMR (400 MHz, DMSO-d6) δ ppm 1.68 (s, 6H) 7.15-7.22 (m, 1H) 7.25-7.33 (m, 3H) 7.36-7.42 (m, 2H) 7.59 (dd, 1H) 7.62-7.68 (m, 1H) 7.68 (dd, 1H) 8.04-8.12 (m, 1H) 8.19 (s, 1H) 8.34 (dd, 1H) 8.51-8.59 (m, 1H) 8.62 (br. s., 1H) 11.37 (br. s., 1H) 11.88 (br. s., 1H) 12.96 (br. s., 1H);

3-{2-[(5-Methyl-2H-pyrazole-3-carbonyl)-amino]-benzoylamino}-1H-thieno[2,3-c]pyrazole-5-carboxylic acid (1-methyl-1-phenyl-ethyl)-amide, [M+H]⁺ 528, ¹H NMR (400 MHz, DMSO-d6) δ ppm 1.67 (s, 6H) 2.29 (s, 3H) 6.52 (s, 1H) 7.13-7.27 (m, 2H) 7.26-7.34 (m, 2H) 7.34-7.42 (m, 2H) 7.55-7.67 (m, 1H) 7.88-8.00 (m, 1H) 8.08 (s, 1H) 8.57-8.70 (m, 2H) 11.28 (br. s., 1H) 11.68 (br. s., 1H) 12.92 (br. s., 1H) 13.05 (br. s., 1H);

3-(2-Acetylamino-benzoylamino)-1H-thieno[2,3-c]pyrazole-5-carboxylic acid (1-methyl-1-phenyl-ethyl)-amide, [M+H]⁺ 462, ¹H NMR (400 MHz, DMSO-d6) δ ppm 1.67 (s, 6H) 2.12 (s, 3H) 7.11-7.26 (m, 2H) 7.27-7.34 (m, 2H) 7.35-7.43 (m, 2H) 7.52-7.61 (m, 1H) 7.82-7.92 (m, 1H) 8.08-8.28 (m, 2H) 8.60 (br. s., 1H) 10.57 (br. s., 1H) 11.21 (br. s., 1H) 12.88 (br. s., 1H);

3-[2-(Tetrahydro-pyran-4-ylamino)-benzoylamino]-1H-thieno[2,3-c]pyrazole-5-carboxylic acid (1-methyl-1-phenyl-ethyl)-amide, [M+H]⁺ 504, ¹H NMR (400 MHz, DMSO-d6) δ ppm 1.35-1.50 (m, 2H) 1.67 (s, 6H) 1.90-2.04 (m, 2H) 3.43-3.55 (m, 2H) 3.61-3.73 (m, 1H) 3.80-3.94 (m, 2H) 6.54-6.69 (m, 1H) 6.82-6.93 (m, 1H) 7.14-7.22 (m, 1H) 7.25-7.33 (m, 2H) 7.33-7.45 (m, 3H) 7.67 (d, J=7.07 Hz, 1H) 7.77-7.87 (m, 1H) 8.08 (s, 1H) 8.60 (br. s., 1H) 10.79 (br. s., 1H) 12.82 (br. s., 1H);

3-[2-(2-Fluoro-benzoylamino)-benzoylamino]-1H-thieno[2,3-c]pyrazole-5-carboxylic acid (1-methyl-1-phenyl-ethyl)-amide, [M+H]⁺ 542, ¹H NMR (400 MHz, DMSO-d6) δ ppm 1.65 (s, 6H) 7.14-7.24 (m, 1H) 7.24-7.44 (m, 7H) 7.57-7.71 (m, 2H) 7.88-7.96 (m, 1H) 7.96-8.03 (m, 1H) 8.07 (s, 1H) 8.47-8.59 (m, 2H) 11.31 (s, 1H) 11.50 (s, 1H) 12.92 (s, 1H);

3-{2-[4-(4-Methyl-piperazin-1-yl)-benzoylamino]-benzoylamino}-1H-thieno[2,3-c]pyrazole-5-carboxylic acid (1-methyl-1-phenyl-ethyl)-amide, [M+H]⁺ 622, ¹H NMR (400 MHz, DMSO-d6) δ ppm 1.66 (s, 6H) 2.21 (s, 3H) 2.33-2.46 (m, 4H) 3.19-3.27 (m, 4H) 7.03 (d, J=9.02 Hz, 1H) 7.14-7.20 (m, 1H) 7.20-7.26 (m, 1H) 7.26-7.32 (m, 2H) 7.34-7.41 (m, 2H) 7.58-7.66 (m, 1H) 7.86 (d, J=9.02 Hz, 1H) 8.04-8.10 (m, 1H) 8.18 (br. s., 1H) 8.62 (br. s., 1H) 8.66-8.71 (m, 1H) 11.36 (br. s., 1H) 11.97 (br. s., 1H) 12.97 (br. s., 1H);

3-[2-(4-Morpholin-4-ylmethyl-benzoylamino)-benzoylamino]-1H-thieno[2,3-c]pyrazole-5-carboxylic acid (1-methyl-1-phenyl-ethyl)-amide, [M+H]⁺ 623;

3-[2-(4-Piperidin-1-ylmethyl-benzoylamino)-benzoylamino]-1H-thieno[2,3-c]pyrazole-5-carboxylic acid (1-methyl-1-phenyl-ethyl)-amide, [M+H]⁺ 621;

3-[2-(4-Pyrrolidin-1-ylmethyl-benzoylamino)-benzoylamino]-1H-thieno[2,3-c]pyrazole-5-carboxylic acid (1-methyl-1-phenyl-ethyl)-amide, [M+H]⁺ 607;

3-[2-(2-Methyl-benzoylamino)-benzoylamino]-1H-thieno[2,3-c]pyrazole-5-carboxylic acid (1-methyl-1-phenyl-ethyl)-amide, [M+H]⁺ 538;

3-[2-(2-Methoxy-benzoylamino)-benzoylamino]-1H-thieno[2,3-c]pyrazole-5-carboxylic acid (1-methyl-1-phenyl-ethyl)-amide, [M+H]⁺ 554;

3-[2-(4-Methyl-benzoylamino)-benzoylamino]-1H-thieno[2,3-c]pyrazole-5-carboxylic acid (1-methyl-1-phenyl-ethyl)-amide, [M+H]⁺ 538;

3-[2-(4-Methoxy-benzoylamino)-benzoylamino]-1H-thieno[2,3-c]pyrazole-5-carboxylic acid (1-methyl-1-phenyl-ethyl)-amide, [M+H]⁺ 554;

3-[2-(4-Fluoro-benzoylamino)-benzoylamino]-1H-thieno[2,3-c]pyrazole-5-carboxylic acid (1-methyl-1-phenyl-ethyl)-amide, [M+H]⁺ 542;

3-{2-[(5-Methyl-2H-pyrazole-3-carbonyl)-amino]-benzoylamino}-1H-thieno[2,3-c]pyrazole-5-carboxylic acid [1-(2-fluoro-phenyl)-1-methyl-ethyl]-amide, [M+H]⁺ 546, ¹H NMR (400 MHz, DMSO-d6) δ ppm 1.72 (s, 6H) 2.28 (s, 3H) 6.52 (s, 1H) 7.02-7.19 (m, 2H) 7.18-7.31 (m, 2H) 7.33-7.43 (m, 1H) 7.56-7.67 (m, 1H) 7.89-7.98 (m, 1H) 8.08 (s, 1H) 8.59-8.72 (m, 2H) 11.27 (br. s., 1H) 11.67 (br. s., 1H) 12.92 (br. s., 1H) 13.06 (br. s., 1H);

3-(2-Acetylamino-benzoylamino)-1H-thieno[2,3-c]pyrazole-5-carboxylic acid [1-(2-fluoro-phenyl)-1-methyl-ethyl]-amide, [M+H]⁺ 480, ¹H NMR (400 MHz, DMSO-d6) δ ppm 1.72 (s, 6H) 2.10 (s, 3H) 7.01-7.16 (m, 2H) 7.17-7.31 (m, 2H) 7.31-7.42 (m, 1H) 7.48-7.60 (m, 1H) 7.79-7.91 (m, 1H) 8.13 (s, 1H) 8.17-8.26 (m, 1H) 8.65 (br. s., 1H) 10.56 (br. s., 1H) 11.18 (br. s., 1H) 12.86 (br. s., 1H);

3-[2-((E)-2-Cyano-3-hydroxy-but-2-enoylamino)-benzoylamino]-1H-thieno[2,3-c]pyrazole-5-carboxylic acid [1-(2-fluoro-phenyl)-1-methyl-ethyl]-amide, [M+H]⁺ 547, ¹H NMR (400 MHz, DMSO-d6) δ ppm 1.74 (s, 6H) 1.95 (s, 3H) 6.95-7.20 (m, 3H) 7.21-7.31 (m, 1H) 7.31-7.44 (m, 2H) 7.43-7.53 (m, 1H) 8.22 (s, 1H) 8.27-8.37 (m, 1H) 8.53 (br. s., 1H) 10.97 (br. s., 1H) 12.04 (br. s., 1H) 12.74 (br. s., 1H);

3-{2-[(Tetrahydro-pyran-4-carbonyl)-amino]-benzoylamino}-1H-thieno[2,3-c]pyrazole-5-carboxylic acid [1-(2-fluoro-phenyl)-1-methyl-ethyl]-amide, [M+H]⁺ 550, ¹H NMR (400 MHz, DMSO-d6) δ ppm 1.59-1.73 (m, 2H) 1.73 (s, 6H) 1.77-1.87 (m, 2H) 2.59-2.72 (m, 1H) 3.34-3.43 (m, 2H) 3.85-3.94 (m, 2H) 7.04-7.19 (m, 2H) 7.19-7.32 (m, 2H) 7.34-7.42 (m, 1H) 7.53-7.62 (m, 1H) 7.89-7.99 (m, 1H) 8.14 (s, 1H) 8.29-8.40 (m, 1H) 8.66 (br. s., 1H) 10.91 (br. s., 1H) 11.23 (br. s., 1H) 12.91 (br. s., 1H);

3-{2-[(5-Methyl-1H-pyrazole-3-carbonyl)-amino]-benzoylamino}-1H-thieno[2,3-c]pyrazole-5-carboxylic acid [1-(2-fluoro-phenyl)-1-methyl-ethyl]-amide, [M+H]⁺ 546;

3-{2-[(Furan-2-carbonyl)-amino]-benzoylamino}-1H-thieno[2,3-c]pyrazole-5-carboxylic acid [1-(2-fluoro-phenyl)-1-methyl-ethyl]-amide, [M+H]⁺ 532;

3-{2-[(2-Ethyl-5-methyl-2H-pyrazole-3-carbonyl)-amino]-benzoylamino}-1H-thieno[2,3-c]pyrazole-5-carboxylic acid [1-(2-fluoro-phenyl)-1-methyl-ethyl]-amide, [M+H]⁺ 574, ¹H NMR (400 MHz, DMSO-d6) δ ppm 1.32 (t, J=7.07 Hz, 3H) 1.73 (s, 6H) 2.21 (s, 3H) 4.46 (q, J=7.19 Hz, 2H) 6.74 (s, 1H) 7.03-7.18 (m, 2H) 7.21-7.35 (m, 2H) 7.34-7.43 (m, 1H) 7.59-7.70 (m, 1H) 8.01-8.11 (m, 1H) 8.19 (s, 1H) 8.43-8.54 (m, 1H) 8.70 (br. s., 1H) 11.34 (br. s., 1H) 11.75 (br. s., 1H) 12.95 (br. s., 1H);

3-[2-((E)-2-Cyano-3-hydroxy-but-2-enoylamino)-4-(4-methyl-piperazin-1-yl)-benzoylamino]-1H-thieno[2,3-c]pyrazole-5-carboxylic acid (1-methyl-1-phenyl-ethyl)-amide hydrochloric salt, [M+H]⁺ 627, ¹H NMR (400 MHz, DMSO-d6) δ ppm 1.69 (s, 6H) 2.30 (s, 3H) 2.86 (s, 3H) 3.01-3.68 (m, 8H) 6.92 (dd, J=8.78, 2.32 Hz, 1H) 7.15-7.23 (m, 1H) 7.27-7.34 (m, 2H) 7.35-7.43 (m, 2H) 8.04 (d, 1H) 8.06 (s, 1H) 8.12 (d, J=2.44 Hz, 1H) 8.20 (s, 1H) 10.38 (br. s., 1H) 11.23 (br. s., 1H) 12.64 (br. s., 1H);

3-{4-(4-Methyl-piperazin-1-yl)-2-[(tetrahydro-pyran-4-carbonyl)-amino]-benzoylamino}-1H-thieno[2,3-c]pyrazole-5-carboxylic acid (1-methyl-1-phenyl-ethyl)-amide, [M+H]+ 630;

3-{4-(4-Methyl-piperazin-1-yl)-2-[(5-methyl-1H-pyrazole-3-carbonyl)-amino]-benzoylamino}-1H-thieno[2,3-c]pyrazole-5-carboxylic acid (1-methyl-1-phenyl-ethyl)-amide, [M+H]+ 626;

3-[2-[(Furan-2-carbonyl)-amino]-4-(4-methyl-piperazin-1-yl)-benzoylamino]-1H-thieno[2,3-c]pyrazole-5-carboxylic acid (1-methyl-1-phenyl-ethyl)-amide, [M+H]+ 612;

3-[2-[(2-Ethyl-5-methyl-2H-pyrazole-3-carbonyl)-amino]-4-(4-methyl-piperazin-1-yl)-benzoylamino]-1H-thieno[2,3-c]pyrazole-5-carboxylic acid (1-methyl-1-phenyl-ethyl)-amide, [M+H]+ 654;

3-{4-(4-Methyl-piperazin-1-yl)-2-[(1H-pyrrole-2-carbonyl)-amino]-benzoylamino}-1H-thieno[2,3-c]pyrazole-5-carboxylic acid (1-methyl-1-phenyl-ethyl)-amide, [M+H]+ 611;

3-[2-((E)-2-Cyano-3-hydroxy-but-2-enoylamino)-4-(4-methyl-piperazin-1-yl)-benzoylamino]-1H-thieno[2,3-c]pyrazole-5-carboxylic acid [1-(2-fluoro-phenyl)-1-methyl-ethyl]-amide, [M+H]+ 645;

3-{4-(4-Methyl-piperazin-1-yl)-2-[(tetrahydro-pyran-4-carbonyl)-amino]-benzoylamino}-1H-thieno[2,3-c]pyrazole-5-carboxylic acid [1-(2-fluoro-phenyl)-1-methyl-ethyl]-amide, [M+H]+ 648;

3-{4-(4-Methyl-piperazin-1-yl)-2-[(5-methyl-1H-pyrazole-3-carbonyl)-amino]-benzoylamino}-1H-thieno[2,3-c]pyrazole-5-carboxylic acid [1-(2-fluoro-phenyl)-1-methyl-ethyl]-amide, [M+H]+ 644;

3-[2-[(Furan-2-carbonyl)-amino]-4-(4-methyl-piperazin-1-yl)-benzoylamino]-1H-thieno[2,3-c]pyrazole-5-carboxylic acid [1-(2-fluoro-phenyl)-1-methyl-ethyl]-amide, [M+H]+ 630;

3-[2-[(2-Ethyl-5-methyl-2H-pyrazole-3-carbonyl)-amino]-4-(4-methyl-piperazin-1-yl)-benzoylamino]-1H-thieno[2,3-c]pyrazole-5-carboxylic acid [1-(2-fluoro-phenyl)-1-methyl-ethyl]-amide, [M+H]+ 672 and 3-{4-(4-Methyl-piperazin-1-yl)-2-[(1H-pyrrole-2-carbonyl)-amino]-benzoylamino}-1H-thieno[2,3-c]pyrazole-5-carboxylic acid [1-(2-fluoro-phenyl)-1-methyl-ethyl]-amide, [M+H]+ 629.

3-{2-[(1H-Pyrrole-2-carbonyl)-amino]-benzoylamino}-1H-thieno[2,3-c]pyrazole-5-carboxylic acid benzylamide, [M+H]+ 485, $^1$H NMR (400 MHz, DMSO-d6) δ ppm 4.45 (d, J=5.85 Hz, 1H) 6.10-6.18 (m, 1H) 6.77-6.85 (m, 1H) 6.95-7.03 (m, 1H) 7.15-7.29 (m, 1H) 7.29-7.39 (m, 5H) 7.54-7.68 (m, 1H) 7.96-8.12 (m, 2H) 8.48-8.60 (m, 1H) 9.18 (br. s., 1H) 11.34 (br. s., 1H) 11.60 (br. s., 1H) 11.81 (br. s., 1H) 12.98 (br. s., 1H);

3-{2-[(1H-Pyrrole-2-carbonyl)-amino]-benzoylamino}-1H-thieno[2,3-c]pyrazole-5-carboxylic acid ((R)-1-phenyl-ethyl)-amide, [M+H]+ 499, $^1$H NMR (400 MHz, DMSO-d6) δ ppm 1.49 (d, J=7.07 Hz, 1H) 5.08-5.19 (m, 1H) 6.13-6.20 (m, 1H) 6.83-6.89 (m, 1H) 6.99-7.04 (m, 1H) 7.16-7.28 (m, 2H) 7.29-7.37 (m, 2H) 7.37-7.43 (m, 2H) 7.57-7.66 (m, 1H) 8.00-8.08 (m, 1H) 8.16 (s, 1H) 8.52-8.60 (m, 1H) 8.98 (d, J=7.93 Hz, 1H) 11.33 (s, 1H) 11.66 (s, 1H) 11.83 (br. s., 1H) 12.97 (s, 1H).

Example 15

3-(2-Nitro-benzoylamino)-thieno[2,3-c]pyrazole-1,5-dicarboxylic Acid 1-ethyl Ester

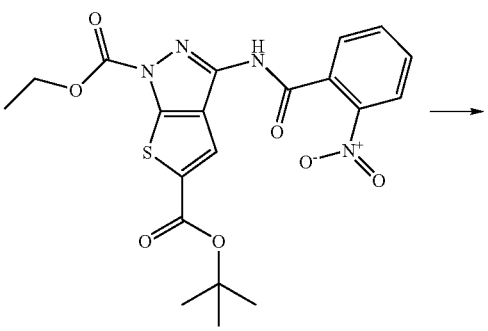

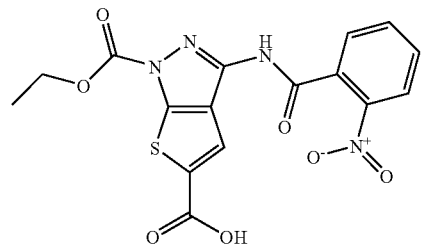

To a solution of 5.380 g of 3-(2-Nitro-benzoylamino)-thieno[2,3-c]pyrazole-1,5-dicarboxylic acid 5-tert-butyl ester 1-ethyl ester in 25 mL of dichloromethane TFA (25 mL) is slowly added at room temperature. After stirring for 1 hour the reaction mixture is dried up. The colourless solid is taken up with ethyl ether and filtered affording 4.052 g (86%) of the titled compound.

LC-MS: Rt 3.12; [M+H]+ 405.

$^1$H NMR (400 MHz, DMSO-D6) δ ppm 1.41 (t, 3H) 4.50 (q, 2H) 7.80-7.95 (m, 3H) 8.06 (s, 1H) 8.19 (dd, 1H) 12.13 (s, 1H) 13.48 (br. s, 1H).

By operating in an analogous way and by using 3-[4-(4-Methyl-piperazin-1-yl)-2-nitro-benzoylamino]-thieno[2,3-c]pyrazole-1,5-dicarboxylic acid 5-tert-butyl ester 1-ethyl ester as the starting material, the following compounds was thus prepared:

3-[4-(4-Methyl-piperazin-1-yl)-2-nitro-benzoylamino]-thieno[2,3-c]pyrazole-1,5-dicarboxylic acid 1-ethyl ester trifluoroacetate.

LC-MS: Rt 2.11; [M+H]+ 503.

$^1$H NMR (400 MHz, DMSO-D6) δ ppm 1.41 (t, 3H) 2.88 (s, 3H) 3.10-3.65 (m, 6H) 4.15 (br. s, 2H) 4.51 (q, 2H) 7.36 (dd 1H) 7.60 (d, 1H) 7.78 (d, 1H) 8.00 (s, 1H) 9.76 (br. s, 1H) 12.01 (s, 1H).

Example 16

5-(1-Methyl-1-phenyl-ethylcarbamoyl)-3-(2-nitro-benzoylamino)-thieno[2,3-c]pyrazole-1-carboxylic Acid ethyl Ester

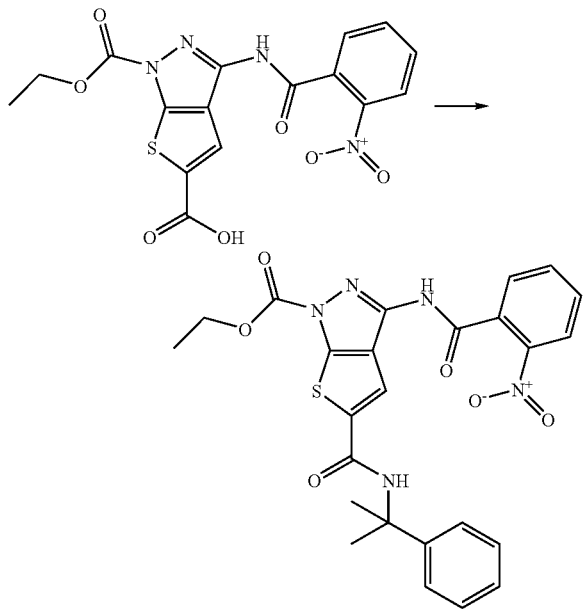

To a solution of 1.995 g (4.93 mmol) of 3-(2-Nitro-benzoylamino)-thieno[2,3-c]pyrazole-1,5-dicarboxylic acid 1-ethyl ester in toluene (35 mL) a total volume of 7.5 ml of $SOCl_2$ was added in a step-wise manner. The suspension so obtained was heated at 80° C. for 7 hours and then evaporated to dryness. The solid was taken up with toluene and dried up twice. Next the solid was dissolved in dichloromethane (30 mL) and added drop-wise to a solution of 1.334 g (9.86 mmol) of cumylamine and DIEA (3.37 mL, 19.73 mmol) in dichloromethane (50 mL) at 0° C. The mixture was stirred and allowed to reach room temperature overnight, washed with 1 N HCl, brine, water, dried up with $Na_2SO_4$ and evaporated to dryness. The crude was then purified by silica gel chromatography (flash chromatography column) eluting with dichloromethane-methanol 99:1. The titled compound was so isolated as a colourless solid (1.80 g 70%).

LC-MS: Rt 6.67; [M+H]+ 522.

$^1$H NMR (400 MHz, DMSO-D6) δ ppm 1.38 (t, 3H) 1.69 (s, 6H) 4.47 (q, 2H) 7.19 (t 1H) 7.31 (t, 2H) 7.39 (d, 2H) 7.77-7.95 (m, 3H) 8.20 (br. d, 1H) 8.38 (s, 1H) 8.94 (s, 1H) 12.09 (s, 1H).

By operating as above reported and by starting from the suitable intermediate derivative, the following compounds were analogously prepared:

5-[1-(2-Fluoro-phenyl)-1-methyl-ethylcarbamoyl]-3-(2-nitro-benzoylamino)-thieno[2,3-c]pyrazole-1-carboxylic acid ethyl ester.

LC-MS: Rt 6.97; [M+H]+ 540;

$^1$H NMR (400 MHz, DMSO-d6) δ ppm 1.38 (d, J=7.07 Hz, 3H) 1.75 (s, 6H) 4.47 (d, J=7.19 Hz, 2H) 7.04-7.19 (m, 2H) 7.21-7.32 (m, 1H) 7.34-7.44 (m, 1H) 7.77-7.87 (m, 2H) 7.87-7.96 (m, 1H) 8.14-8.27 (m, 1H) 8.38 (s, 1H) 9.02 (s, 1H) 12.08 (s, 1H);

5-(1-Methyl-1-phenyl-ethylcarbamoyl)-3-[4-(4-methyl-piperazin-1-yl)-2-nitro-benzoylamino]-thieno[2,3-c]pyrazole-1-carboxylic acid ethyl ester, [M+H]+ 620, $^1$H NMR (400 MHz, DMSO-d6) δ ppm 1.38 (d, J=7.07 Hz, 3H) 1.68 (s, 6H) 2.28 (s, 3H) 2.39-2.60 (m, 4H) 3.36-3.47 (m, 4H) 4.48 (d, J=7.07 Hz, 2H) 7.15-7.23 (m, 1H) 7.24-7.34 (m, 2H) 7.35-7.43 (m, 2H) 7.46-7.50 (m, 1H) 7.61-7.77 (m, 1H) 8.29 (s, 1H) 8.91 (s, 1H) 11.88 (s, 1H);

5-(1-Methyl-1-phenyl-ethylcarbamoyl)-3-(2-nitro-4-pyrrolidin-1-ylmethyl-benzoylamino)-thieno[2,3-c]pyrazole-1-carboxylic acid ethyl ester, [M+H]+ 605, $^1$H NMR (400 MHz, DMSO-d6) δ ppm 1.38 (d, J=7.07 Hz, 3H) 1.69 (s, 6H) 1.72-1.82 (m, 4H) 2.40-2.60 (m, 4H) 3.78 (s, 2H) 4.49 (d, J=7.07 Hz, 2H) 7.16-7.22 (m, 1H) 7.27-7.34 (m, 2H) 7.36-7.43 (m, 2H) 7.74-7.85 (m, 2H) 8.06-8.12 (m, 1H) 8.37 (s, 1H) 8.94 (s, 1H) 12.05 (s, 1H);

5-(1-Methyl-1-phenyl-ethylcarbamoyl)-3-(2-nitro-4-piperidin-1-ylmethyl-benzoylamino)-thieno[2,3-c]pyrazole-1-carboxylic acid ethyl ester, [M+H]+ 619, $^1$H NMR (400 MHz, DMSO-d6) δ ppm 1.38 (d, J=7.07 Hz, 3H) 1.41-1.47 (m, 2H) 1.50-1.61 (m, 4H) 1.69 (s, 6H) 2.35-2.45 (m, 4H) 3.62 (s, 2H) 4.47 (d, J=7.19 Hz, 2H) 7.14-7.24 (m, 1H) 7.26-7.35 (m, 2H) 7.36-7.43 (m, 2H) 7.74-7.86 (m, 2H) 8.05-8.12 (m, 1H) 8.37 (s, 1H) 8.94 (s, 1H) 12.03 (s, 1H);

5-(1-Methyl-1-phenyl-ethylcarbamoyl)-3-(4-morpholin-4-ylmethyl-2-nitro-benzoylamino)-thieno[2,3-c]pyrazole-1-carboxylic acid ethyl ester, [M+H]+ 621, $^1$H NMR (400 MHz, DMSO-d6) δ ppm 1.38 (t, J=7.07 Hz, 3H) 1.69 (s, 6H) 3.25-3.75 (m, 4H) 3.85 (br. s., 2H) 3.96 (br. s., 2H) 4.48 (q, J=7.03 Hz, 2H) 4.56 (br. s., 1H) 7.16-7.22 (m, 1H) 7.27-7.34 (m, 2H) 7.36-7.43 (m, 2H) 7.92 (d, J=7.93 Hz, 1H) 8.17 (br. s., 1H) 8.37 (s, 1H) 8.54 (br. s., 1H) 8.95 (s, 1H) 9.12 (br. s., 1H) 11.82 (br. s., 1H) 12.13 (s, 1H);

5-[1-(2-Fluoro-phenyl)-1-methyl-ethylcarbamoyl]-3-[4-(4-methyl-piperazin-1-yl)-2-nitro-benzoylamino]-thieno[2,3-c]pyrazole-1-carboxylic acid ethyl ester, [M+H]+ 638.

Example 17

3-(2-Amino-benzoylamino)-5-(1-methyl-1-phenyl-ethylcarbamoyl)-thieno[2,3-c]pyrazole-1-carboxylic Acid ethyl Ester

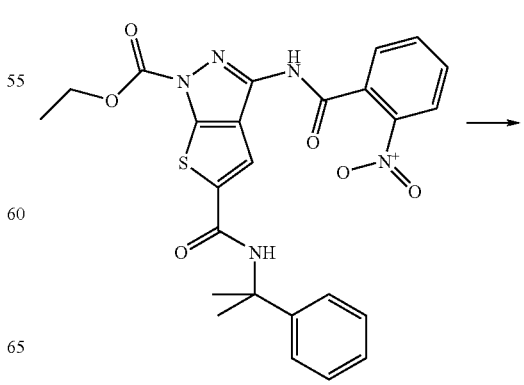

-continued

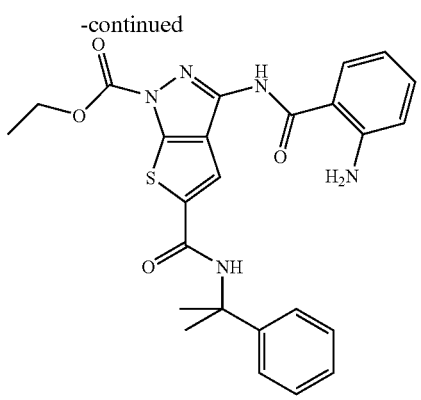

The suspension of 1.8 g (3.451 mmol) of 5-(1-Methyl-1-phenyl-ethylcarbamoyl)-3-(2-nitro-benzoylamino)-thieno[2,3-c]pyrazole-1-carboxylic acid ethyl ester and 500 mg of Pd/C (10%) in 45 mL of ethylacetate was shaken under hydrogen pressure (40 psi). The catalyst was renewed (500 mg) after 8 hours and the mixture treated for further 8 hours. The catalyst was then filtered over a celite pad and the solvent removed under vacuum. The crude was purified on silica gel (eluant dichloromethane-methanol 98:2) yielding 1.44 g (85%) of the title compound.

LC-MS: Rt 7.12; [M+H]$^+$ 492, $^1$H NMR (400 MHz, DMSO-d6) δ ppm 1.39 (d, J=7.07 Hz, 3H) 1.69 (s, 6H) 4.48 (d, J=7.07 Hz, 2H) 6.53-6.63 (m, 1H) 6.69 (br. s., 2H) 6.77-6.83 (m, 1H) 7.14-7.35 (m, 4H) 7.36-7.43 (m, 2H) 7.78-7.88 (m, 1H) 8.28 (s, 1H) 8.80 (s, 1H) 11.33 (br. s., 1H).

By operating as above reported and by starting from the suitable intermediate derivative, the following compounds were analogously prepared:

3-(2-Amino-benzoylamino)-5-[1-(2-fluoro-phenyl)-1-methyl-ethylcarbamoyl]-thieno[2,3-c]pyrazole-1-carboxylic acid ethyl ester, [M+H]$^+$ 510, $^1$H NMR (400 MHz, DMSO-d6) δ ppm 1.39 (d, J=7.07 Hz, 3H) 1.75 (s, 6H) 4.48 (d, J=7.07 Hz, 2H) 6.53-6.62 (m, 1H) 6.69 (br. s., 2H) 6.78-6.85 (m, 1H) 7.04-7.19 (m, 2H) 7.20-7.32 (m, 2H) 7.34-7.44 (m, 1H) 7.78-7.87 (m, 1H) 8.27 (s, 1H) 8.87 (s, 1H) 11.33 (br. s., 1H);

3-[2-Amino-4-(4-methyl-piperazin-1-yl)-benzoylamino]-5-(1-methyl-1-phenyl-ethylcarbamoyl)-thieno[2,3-c]pyrazole-1-carboxylic acid ethyl ester, [M+H]$^+$ 590.

3-[2-Amino-4-(4-methyl-piperazin-1-yl)-benzoylamino]-5-[1-(2-fluoro-phenyl)-1-methyl-ethylcarbamoyl]-thieno[2,3-c]pyrazole-1-carboxylic acid ethyl ester, [M+H]$^+$ 608.

The invention claimed is:
1. A compound of formula (I):

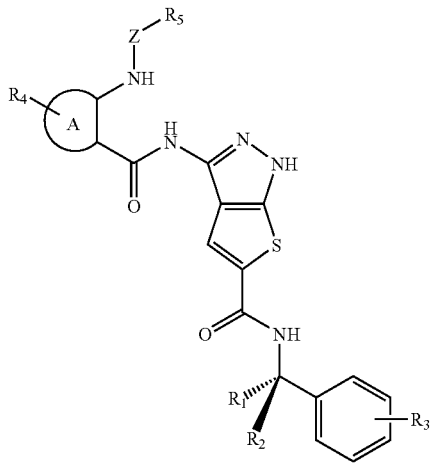

wherein
A is an aryl or heteroaryl ring, on which the substituent —NHZR$_5$ is at the ortho position to the CONH linker;
R$_1$ and R$_2$ are the same or different and, independently from each other, represent a hydrogen atom or a straight or branched C$_1$-C$_3$ alkyl or

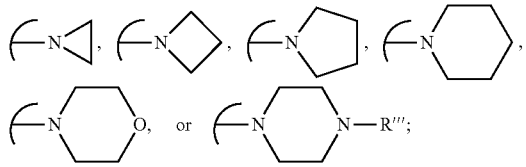

R$_3$ is a hydrogen or halogen atom or a group selected from hydroxy, cyano, straight or branched C$_1$-C$_3$ alkyl, C$_1$-C$_6$ alkylamino, C$_1$-C$_6$ di-alkylamino and C$_1$-C$_3$ alkoxy;
R$_4$ is a hydrogen or halogen atom or a group selected from hydroxy, straight or branched C$_1$-C$_3$ alkyl, C$_1$-C$_3$ alkoxy, C$_1$-C$_6$ alkylamino, C$_1$-C$_6$ dialkylamino, azetidin-1-yl, pyrrolidin-1-yl, piperidin-1-yl, (1-methyl-piperazin-4-yl), (morpholino-4-yl), (azetidin-1-yl)methyl, (pyrrolidin-1-yl)methyl, (piperidin-1-yl)methyl, (1-methyl-piperazin-4-yl)methyl, (morpholino-4-yl)methyl, (1-methyl-piperidin-4-yloxy)methyl, (C$_1$-C$_6$ alkylamino)methyl and (C$_1$-C$_6$ di-alkylamino)methyl;
Z is direct bond, >C=O or —C(=O)NH—;
R$_5$ is hydrogen or an optionally substituted group selected from C$_1$-C$_6$ alkyl, C$_3$-C$_6$ cycloalkyl, C$_2$-C$_6$ alkenyl, aryl, heteroaryl and saturated heteroaryl;
or optical isomers, tautomers, or pharmaceutically acceptable salts thereof.

2. A compound of formula (I) as defined in claim 1 wherein A is a group selected from thienyl, furyl, pyrrolyl and phenyl.
3. A compound of formula (I) as defined in claim 1 or 2 wherein A is a phenyl ring substituted at position 2 by NH—Z—R$_5$ and substituted at position 4 by a group R$_4$ chosen from hydrogen, halogen, methoxy, azetidin-1-yl, pyrrolidin-1-yl, piperidin-1-yl, (1-methyl-piperazin-4-yl), (morpholino-4-yl), (azetidin-1-yl)methyl, (pyrrolidin-1-yl)methyl, (piperidin-1-yl)methyl, (1-methyl-piperazin-4-yl)methyl, (morpholino-4-yl)methyl, (1-methyl-piperidin-4-yloxy)methyl, (C$_1$-C$_6$ alkylamino)methyl and (C$_1$-C$_6$ di-alkylamino)methyl.
4. A compound of formula (I) as defined in any one of claims 1, 2 and 3 wherein Z is >C=O.
5. A compound of formula (I) as defined in claim 1 wherein R$_1$ and R$_2$ are both a methyl group.
6. A compound of formula (I) as defined in claim 1 wherein R$_3$ represents a hydrogen or halogen atom.
7. A compound as defined in claim 1, optionally in the form of a pharmaceutically acceptable salt thereof, which is 3-{2-[(1H-Pyrrole-2-carbonyl)-amino]-benzoylamino}-1H-thieno[2,3-c]pyrazole-5-carboxylic acid (1-methyl-1-phenyl-ethyl)-amide or 3-{2-[(1H-Pyrrole-2-carbonyl)-amino]-benzoylamino}-1H-thieno[2,3-c]pyrazole-5-carboxylic acid [1-(2-fluoro-phenyl)-1-methyl-ethyl]-amide.
8. A compound or a pharmaceutically acceptable salt thereof which is selected from the group consisting of:
   i. 3-{2-[(5-Methyl-isoxazole-4-carbonyl)-amino]-benzoylamino}-1H-thieno[2,3-c]pyrazole-5-carboxylic acid (1-methyl-1-phenyl-ethyl)-amide;
   ii. 3-{2-[(tetrahydro-pyran-4-carbonyl)-amino]-benzoylamino}-1H-thieno[2,3-c]pyrazole-5-carboxylic acid (1-methyl-1-phenyl-ethyl)-amide;
   iii. 3-{2-[(5-methyl-1H-pyrazole-3-carbonyl)-amino]-benzoylamino}-1H-thieno[2,-3-c]pyrazole-5-carboxylic acid (1-methyl-1-phenyl-ethyl)-amide;
   iv. 3-{2-[(furan-2-carbonyl)-amino]-benzoylamino}-1H-thieno[2,3-c]pyrazole-5-carboxylic acid (1-methyl-1-phenyl-ethyl)-amide;
   v. 3-{2-[(2-ethyl-5-methyl-2H-pyrazole-3-carbonyl)-amino]-benzoylamino}-1H-thieno[2,3-c]pyrazole-5-carboxylic acid (1-methyl-1-phenyl-ethyl)-amide;
   vi. 3-{2-[(5-methyl-isoxazole-4-carbonyl)-amino]-benzoylamino}-1H-thieno[2,3-c]pyrazole-5-carboxylic acid [1-(2-fluoro-phenyl)-1-methyl-ethyl]-amide;
   vii. 3-{2-[(tetrahydro-pyran-4-carbonyl)-amino]-benzoylamino}-1H-thieno[2,3-c]pyrazole-5-carboxylic acid [1-(2-fluoro-phenyl)-1-methyl-ethyl]-amide;
   viii. 3-{2-[(5-methyl-1H-pyrazole-3-carbonyl)-amino]-benzoylamino}-1H-thieno[2,3-c]pyrazole-5-carboxylic acid [1-(2-fluoro-phenyl)-1-methyl-ethyl]-amide;
   ix. 3-{2-[(furan-2-carbonyl)-amino]-benzoylamino}-1H-thieno[2,3-c]pyrazole-5-carboxylic acid [1-(2-fluoro-phenyl)-1-methyl-ethyl]-amide;
   x. 3-{2-[(2-ethyl-5-methyl-2H-pyrazole-3-carbonyl)-amino]-benzoylamino}-1H-thieno[2,3-c]pyrazole-5-carboxylic acid [1-(2-fluoro-phenyl)-1-methyl-ethyl]-amide;
   xi. 3-[2-[(5-methyl-isoxazole-4-carbonyl)-amino]-4-(4-methyl-piperazin-1-yl)-benzoylamino]-1H-thieno[2,3-c]pyrazole-5-carboxylic acid (1-methyl-1-phenyl-ethyl)-amide;
   xii. 3-{4-(4-methyl-piperazin-1-yl)-2-[(tetrahydro-pyran-4-carbonyl)-amino]-benzoylamino}-1H-thieno[2,3-c]pyrazole-5-carboxylic acid (1-methyl-1-phenyl-ethyl)-amide;
   xiii. 3-{4-(4-methyl-piperazin-1-yl)-2-[(5-methyl-1H-pyrazole-3-carbonyl)-amino-]-benzoylamino}-1H-thieno[2,3-c]pyrazole-5-carboxylic acid (1-methyl-1-phenyl-ethyl)-amide;
   xiv. 3-[2-[(furan-2-carbonyl)-amino]-4-(4-methyl-piperazin-1-yl)-benzoylamino]-1H-thieno[2,3-c]pyrazole-5-carboxylic acid (1-methyl-1-phenyl-ethyl)-amide;

xv. 3-[2-[(2-ethyl-5-methyl-2H-pyrazole-3-carbonyl)-amino]-4-(4-methyl-piperazin-1-yl)-benzoylamino]-1H-thieno[2,3-c]pyrazole-5-carboxylic acid (1-methyl-1-phenyl-ethyl)-amide;

xvi. 3-{4-(4-methyl-piperazin-1-yl)-2-[(1H-pyrrole-2-carbonyl)-amino]-benzoylamino}-1H-thieno[2,3-c]pyrazole-5-carboxylic acid (1-methyl-1-phenyl-ethyl)-amide;

xvii. 3-[2-[(5-methyl-isoxazole-4-carbonyl)-amino]-4-(4-methyl-piperazin-1-yl)-benzoylamino]-1H-thieno[2,3-c]pyrazole-5-carboxylic acid [1-(2-fluoro-phenyl)-1-methyl-ethyl]-amide;

xviii. 3-{4-(4-methyl-piperazin-1-yl)-2-[(tetrahydro-pyran-4-carbonyl)-amino]-benzoylamino}-1H-thieno[2,3-c]pyrazole-5-carboxylic acid [1-(2-fluoro-phenyl)-1-methyl-ethyl]-amide;

xix. 3-{4-(4-methyl-piperazin-1-yl)-2-[(5-methyl-1H-pyrazole-3-carbonyl)-amino-]-benzoylamino}-1H-thieno[2,3-c]pyrazole-5-carboxylic acid [1-(2-fluoro-phenyl)-1-methyl-ethyl]-amide;

xx. 3-[2-[(furan-2-carbonyl)-amino]-4-(4-methyl-piperazin-1-yl)-benzoylamino]-1H-thieno[2,3-c]pyrazole-5-carboxylic acid [1-(2-fluoro-phenyl)-1-methyl-ethyl]-amide;

xxi. 3-[2-[(2-ethyl-5-methyl-2H-pyrazole-3-carbonyl)-amino]-4-(4-methyl-piperazin-1-yl)-benzoylamino]-1H-thieno[2,3-c]pyrazole-5-carboxylic acid [1-(2-fluoro-phenyl)-1-methyl-ethyl]-amide and xxii. 3-{4-(4-methyl-piperazin-1-yl)-2-[(1H-pyrrole-2-carbonyl)-amino]-benzoylamino}-1H-thieno[2,3-c]pyrazole-5-carboxylic acid [1-(2-fluoro-phenyl)-1-methyl-ethyl]-amide.

9. A process for preparing a compound of formula (I) as defined in claim 1, which process comprises:

a) reacting a compound of formula (II),

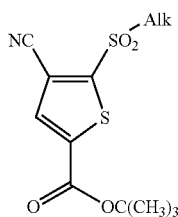

(II)

wherein Alk represents a straight or branched $C_1$-$C_6$ alkyl group, with hydrazine or a hydrazine salt and treating the resultant tert-butyl 4-cyano-5-hydrazinothiophene-2-carboxylate intermediate under acidic condition;

b) reacting the resultant cyclized compound of formula (III)

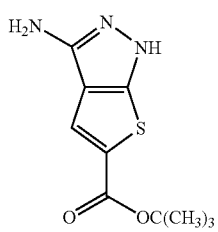

(III)

with any suitable pyrazole nitrogen atom protecting agent, c) acylating the resultant compound of formula (IV)

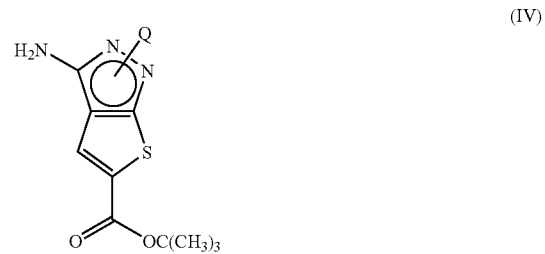

(IV)

wherein Q represents the said protecting group with a compound of formula (V)

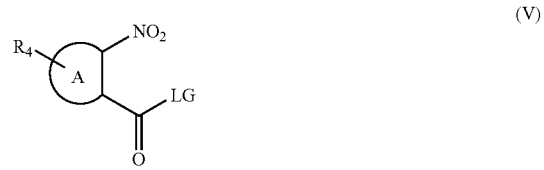

(V)

wherein A and $R_4$ are as defined in claim 1 and LG represents a suitable leaving group, d) reducing the nitro group of the resultant compound of formula (VI)

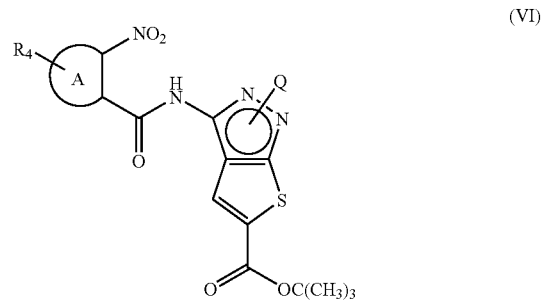

(VI)

wherein A, $R_4$ and Q are as defined above, and
either
e) acylating the resultant compound of formula (VII)

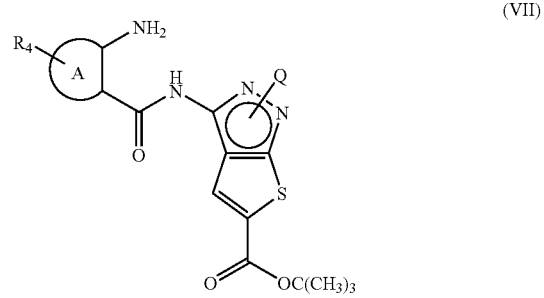

(VII)

wherein A, $R_4$ and Q are as defined above, with a compound of formula $R_5$—Z-LG (VIII) or $R_5$—NCO (IX), when Z is >C═O or —C(═O)NH—, and $R_5$ is as defined in claim 1 and LG is as above defined; so as to obtain a compound of formula (X)

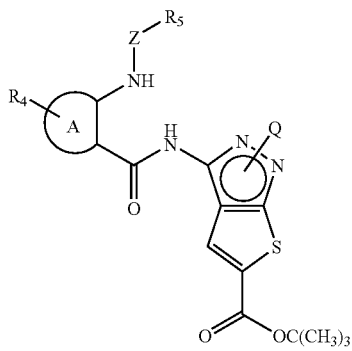

wherein A, $R_4$, $R_5$ and Q are as defined above, and Z is >C=O or —C(=O)NH—; or e') treating a compound of formula (VII) as defined above with a carbonyl compound of formula W—CO—Y (XI) wherein W and Y are hydrogen atoms or an optionally substituted group selected from $C_1$-$C_5$ alkyl, $C_1$-$C_5$ cycloalkyl, aryl, heteroaryl or saturated heteroaryl, in the presence of an opportune reducing agent, so as to obtain a compound of formula (X) as above defined wherein Z is a direct bond and f) selectively hydrolyzing the tert-butyl ester group of the resultant compound of formula (X) as defined above;

g) reacting the resultant compound of formula (XII)

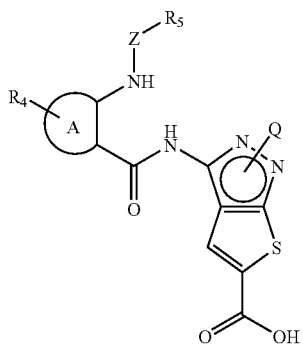

wherein A, $R_4$, $R_5$ and Q are as defined above, and Z is as defined in claim 1, with a compound of formula (XIII)

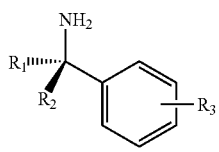

wherein $R_1$, $R_2$ and $R_3$ are as defined in claim 1, in the presence of any suitable condensing agent, and i) deprotecting the resultant compound of formula (XIV) by removing the Q pyrazole nitrogen atom protecting group:

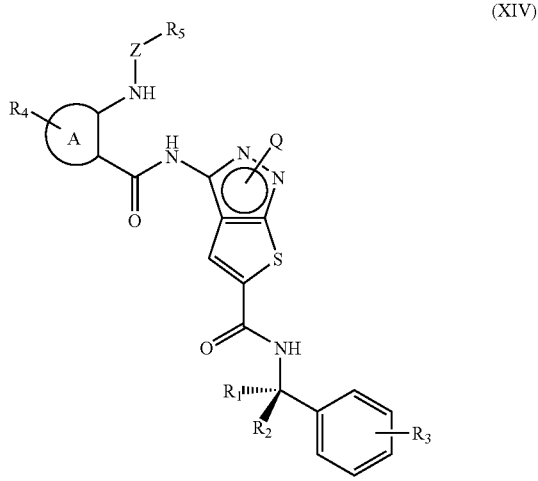

wherein A, $R_1$, $R_2$, $R_3$, $R_4$, $R_5$, Q and Z are as defined above so as to obtain a compound of formula (I) as defined in claim 1 and, whenever desired, converting the resultant compound of formula (I) as defined above into a different compound of formula (I) by well known reactions and if wanted, converting the compound of formula (I) as defined above into a pharmaceutically acceptable salt or converting the salt thereof into the free compound of formula (I) as defined above.

10. A process for preparing a compound of formula (I) as defined in claim 1, which process comprises:

j) selectively hydrolyzing the tert-butyl ester group of the compound of formula (VI) as defined in claim 9;

k) reacting the resultant compound of formula (XV)

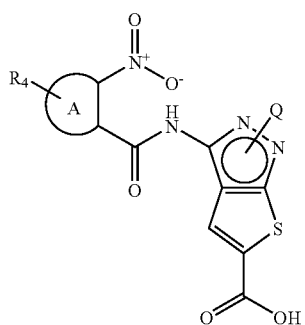

wherein A, $R_4$ and Q are as defined in claim 1, with a compound of formula (XIII) as defined in claim 9, in the presence of any suitable condensing agent, and l) reducing the nitro group of the resultant compound of formula (XVI)

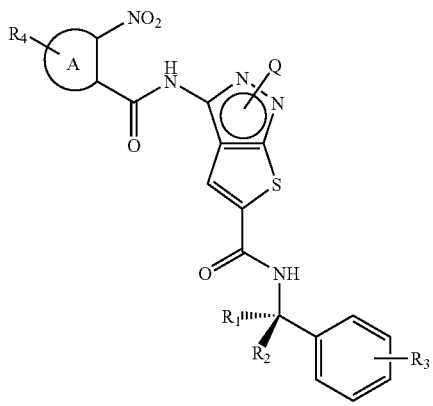

(XVI)

wherein A, $R_1$, $R_2$, $R_3$, $R_4$ and Q are as defined in claim 9, and either m) acylating the resultant compound of formula (XVII)

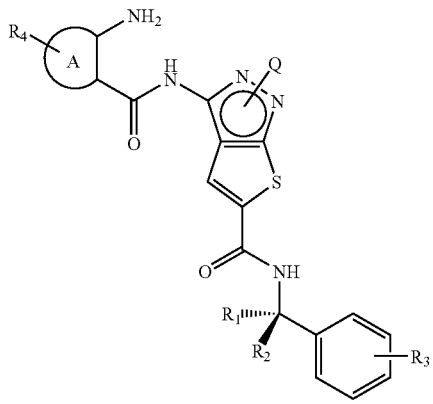

(XVII)

wherein A, $R_1$, $R_2$, $R_3$, $R_4$ and Q are as defined above, with a compound of formula $R_5$—Z-LG (VIII) or $R_5$—NCO (IX), when Z is >C=O or —C(=O)NH—, and $R_5$ and LG are as defined in claim 9; so as to obtain a compound of formula (XIV) as defined in claim 9 wherein Z is >C=O or —C(=O)NH—;or m') treating a compound of formula (XVII) as defined above with a carbonyl compound of formula (XI) as defined in claim 9, in the presence of an opportune reducing agent, so as to obtain a compound of formula (XIV) as above defined wherein Z is a direct bond and finally deprotecting the resultant compound of formula (XIV) as described in claim 9 under step i).

11. A method for treating cancer selected from melanoma, ovarian carcinoma, AML, colorectal cancer, and breast cancer in a mammal which comprises administering to said mammal in need thereof an effective amount of a compound of formula (I) as defined in claim 1.

12. The method according to claim 11 further comprising subjecting the mammal in need thereof to a radiation therapy or chemotherapy regimen in combination with at least one cytostatic or cytotoxic agent.

13. The method according to claim 11 wherein the mammal in need thereof is a human.

14. A method for inhibiting Aurora 2 kinase activity which comprises contacting the said kinase with an effective amount of a compound as defined in claim 1.

15. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

16. A pharmaceutical composition according to claim 15 further comprising one or more chemotherapeutic agents.

17. A product or kit comprising a compound of formula (I) or a pharmaceutically acceptable salt thereof, as defined in claim 11, or pharmaceutical compositions thereof.

18. A compound of formula (I) or a pharmaceutically acceptable salt thereof, as defined in claim 1, for use as a medicament.

* * * * *

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: carboxy-terminally biotinylated peptide

<400> SEQUENCE: 1

Lys Lys Lys Ser Pro Gly Glu Tyr Val Asn Ile Glu Phe Gly Gly Gly
1               5                   10                  15

Gly Gly Lys

<210> SEQ ID NO 2
<211> LENGTH: 7
<212> TYPE: PRT
<213> ORGANISM: Artificial Sequence
<220> FEATURE:
<223> OTHER INFORMATION: biotinylated peptide

<400> SEQUENCE: 2

Leu Arg Arg Trp Ser Leu Gly
1               5
```